US006896687B2

(12) United States Patent
Dakov

(10) Patent No.: US 6,896,687 B2
(45) Date of Patent: *May 24, 2005

(54) CONNECTORS FOR HOLLOW ANATOMICAL STRUCTURES AND METHODS OF USE

(76) Inventor: Pepi Dakov, 62-60 99th St., Apt. 1227, Rego Park, NY (US) 11374

( * ) Notice: Subject to any disclaimer, the term of this patent is extended or adjusted under 35 U.S.C. 154(b) by 564 days.

This patent is subject to a terminal disclaimer.

(21) Appl. No.: 09/896,542

(22) Filed: Jun. 29, 2001

(65) Prior Publication Data

US 2001/0039425 A1 Nov. 8, 2001

Related U.S. Application Data

(63) Continuation-in-part of application No. 09/479,792, filed on Jan. 8, 2000, now Pat. No. 6,254,618, which is a continuation-in-part of application No. 08/858,275, filed on May 19, 1997, now Pat. No. 6,030,392.

(51) Int. Cl.⁷ .............................................. A61B 17/04
(52) U.S. Cl. ..................................................... 606/153
(58) Field of Search ......................................... 606/153

(56) References Cited

U.S. PATENT DOCUMENTS

| 4,352,358 | A |   | 10/1982 | Angelchik ............... 128/334 R |
|-----------|---|---|---------|------------------------------------|
| 4,368,736 | A |   | 1/1983  | Kaster .................... 128/334 C |
| 4,535,483 | A |   | 8/1985  | Klawitter .................. 623/2 |
| 4,650,486 | A |   | 3/1987  | Chareire ................... 623/3 |
| 4,854,316 | A |   | 8/1989  | Davis ..................... 128/334 R |
| 5,123,908 | A | * | 6/1992  | Chen ......................... 606/153 |
| 5,234,447 | A |   | 8/1993  | Kaster ....................... 606/153 |
| 5,336,233 | A |   | 8/1994  | Chen ......................... 606/153 |
| 5,366,462 | A |   | 11/1994 | Kaster ....................... 606/153 |
| 5,403,333 | A |   | 4/1995  | Kaster ....................... 606/151 |
| 5,456,714 | A |   | 10/1995 | Owen .......................... 623/1 |
| 5,486,187 | A |   | 1/1996  | Schenck ..................... 606/153 |
| 5,540,701 | A |   | 7/1996  | Sharkey ..................... 606/153 |
| 5,752,966 | A |   | 5/1998  | Chang ........................ 606/151 |
| 5,868,763 | A |   | 2/1999  | Spence ...................... 606/153 |
| 5,916,226 | A |   | 6/1999  | Tozzi ........................ 606/153 |
| 5,972,017 | A |   | 10/1999 | Berg ......................... 606/198 |
| 5,976,178 | A |   | 11/1999 | Goldsteen .................... 623/1 |
| 6,001,124 | A |   | 12/1999 | Bachinski .................... 623/1 |
| 6,036,704 | A | * | 3/2000  | Yoon ......................... 606/153 |
| 6,068,654 | A |   | 5/2000  | Berg ........................... 623/1 |
| 6,113,612 | A |   | 9/2000  | Swanson ..................... 606/153 |
| 6,120,432 | A |   | 9/2000  | Sullivan ...................... 600/36 |
| 6,152,937 | A |   | 11/2000 | Peterson .................... 606/153 |
| 6,152,945 | A |   | 11/2000 | Bachinski ................... 606/198 |
| 6,171,321 | B1 |  | 1/2001  | Gifford ...................... 606/153 |
| 6,179,848 | B1 |  | 1/2001  | Solem ....................... 606/153 |
| 6,179,849 | B1 |  | 1/2001  | Yencho ...................... 606/153 |
| 6,186,942 | B1 |  | 2/2001  | Sullivan ...................... 600/36 |
| 6,190,397 | B1 |  | 2/2001  | Spence ...................... 606/153 |
| 6,193,734 | B1 |  | 2/2001  | Bolduc ...................... 606/153 |
| 6,241,743 | B1 |  | 6/2001  | Levin ........................ 606/153 |
| 6,293,965 | B1 |  | 9/2001  | Berg ........................ 623/1.13 |
| 6,302,905 | B1 |  | 10/2001 | Goldsteen ................... 623/1.1 |
| 6,309,416 | B1 |  | 10/2001 | Swanson .................... 623/1.23 |

\* cited by examiner

*Primary Examiner*—Gary Jackson

(57) ABSTRACT

The connector consists of an annular rigid body conformed to an outer surface around a wall-opening of a hollow anatomical structure and holding means that keep the hollow structure adjoined internally to the annular body, wherein a union of the annular body with another annular body of another connector attached to another hollow structure forms an inner fluidproof surface that surrounds the abutted cut-edges of the wall-openings of the approximated two hollow structures. Different embodiments of end connectors and side connectors in divisible or indivisible unions are provided for end-to-end and side-to-end anastomoses of various hollow structures.

23 Claims, 23 Drawing Sheets

CONNECTORS FOR HOLLOW ANATOMICAL STRUCTURES AND METHODS OF USE

This is a continuation-in-part application of U.S. patent application Ser. No. 09/479,792 from Jan. 8, 2000, now U.S. Pat. No. 6,254,618 which is a continuation-in-part of U.S. patent application Ser. No. 08/858,275 from May 19, 1997 now a U.S. Pat. No. 6,030,392 from Feb. 29, 2000.

FIELD OF THE INVENTION

This invention pertains to devices for joining hollow anatomical structures and more specifically to connectors for hollow anatomical structures.

BACKGROUND OF THE INVENTION

The most important and difficult part of the work of the surgeon is to perform anastomoses of hollow anatomical organs. At the end of the twentieth century, most of the surgical anastomoses are still performed in same way as hundred years ago—by manual suturing.

Blood vessels are anastomosed by multiple manually placed stitches. The surgical procedure is time consuming and demands highly specialized skills. This is associated with a substantial rate of complications due to ischemia in the tissues suffering from the interrupted blood supply during the procedure. Bleeding frequently occurs from the suture lines. Remaining blood clots and persistent drains increase the chances for development of infections. Subjective technical mistakes by the surgeon can result in stenosis or thrombosis of the anastomosis.

Anastomoses of gastrointestinal organs have been automated to some extent by circular staplers. In brief, their method of operation is: first, an anvil and a stapling cartridge are introduced inside the ends of two hollow organs through a side slit of one of them; second, the ends of the two organs are inverted between the stapling cartridge and the anvil by two manual sutures; and third, multiple staples are ejected axially from the cartridge, they pierce the inverted walls of the two organs and are clinched by the anvil.

Circular staples have proven to perform more reliable anastomoses as compared to these accomplished by manual stitches. Still, their benefit is outweighed by several drawbacks. First, the time needed to complete the anastomosis is not actually reduced as the surgeon has to place two manual sutures to invert the ends of the two organs and after that has to suture manually the incisional slit. Second, the higher risk of technical failure associated with the process of manual suturing remains present as the surgeon has to close the incisional slit by multiple hand stitches. And third, the application of circular staples is limited only to relatively large organs, such as the intestines and the stomach.

Joining of hollow anatomical organs with artificial structures is also difficult as performed by the current surgical methods. That is particularly problematic for intestinal organs, for which there are no reliable methods for joining with artificial structures.

It is evident, that development of devices and methods for quick, easy, and reliable anastomoses of hollow anatomical organs is extremely important for reducing the complications and improving the outcome in many surgical procedures, especially in cardiovascular surgery.

Various stapling devices have been proposed for implementation with blood vessels. Most of them are based on a similar method of operation as that of circular staplers—to suture the ends of blood vessels by axially ejected staples. The walls of blood vessels cannot be inverted (as the walls of gastrointestinal organs) because this will impede the blood flow. For that reason, blood vessels are either everted or cuffed before being stapled by the proposed stapling devices. Everting or cuffing body organs is more difficult and time consuming to perform than inverting. This is particularly true for blood vessels, which in general are located in less accessible places and have more rigid walls than intestines. Sometimes, this is even impossible to perform sometimes when the vessels are with substantially rigid walls (such as arteries with atherosclerotic changes). For these reasons, none of these stapling devices for blood vessels has established a practical application.

A device for accomplishing anastomoses of blood vessels, without changing their natural configurations, by ejecting staples in radial direction, is described by Perouse (U.S. Pat. No. 5,346,115). The described device has several important limitations. It can be used only for attachment of a non-rigid graft to the internal surface of a blood vessel. The internally attached graft narrows the lumen of the vessel. This limits the application of the device only to relatively large vessels. Direct anastomosis (without a graft) of two blood vessels cannot be accomplished. The device can be used only for end-to-end anastomosis. Side-to-end anastomosis cannot be performed.

A side-to-end vascular staple apparatus and method of stapling is described by Kaster et al. in U.S. Pat. No. 5,234,447, in U.S. Pat. No. 5,366,452, and in U.S. Pat. No. 5,403,333. In the described method, one of the vessels is inserted through a mandrel and cuffed over the end of the mandrel. The procedure can be performed only if the other end of the vessel is loose, as the mandrel has to be withdrawn back after the completion of the procedure. Therefore, the staple apparatus can be used to anastomose only the first end of a vessel graft. It cannot be used to anastomose the second end of the graft because the mandrel cannot be withdrawn after the first end is joined. This is a major practical limitation of the described apparatus and method. Furthermore, the diameter of the staple apparatus, after the interior engagement members are bent, is larger than the diameter of the side opening. This makes difficult the insertion of the staple apparatus into the vessel. Deforming the internal engagement members consequently one by one slows additionally the anastomosing procedure. And finally, the end-anastomosed vessel needs to be cuffed in order to perform the procedure. As explained above, this is an important limitation for the practical application of the described apparatus and method.

Many authors have proposed various types of rigid connectors for performing quick anastomoses of hollow organs. While the connectors differ much in structures and forms, their method of operation is principally the same. Two hollow body organs become joined by compressing their flanged (everted or inverted) or cuffed walls between the rigid surfaces of two coupled connectors.

Compressing body organs between rigid connectors is associated with a very high risk of serious complication. Applying a constant pressure on a substantially large area of body tissues produces adverse changes in the tissues. The compressed tissues suffer ischemic changes due to the decreased blood-oxygen supply. A high pressure deprives the tissues from blood-oxygen supply. This results in a necrosis, which may lead to rupture of the anastomosed organs. A moderate pressure diminishes the blood-oxygen supply. This slows the metabolism and the regeneration of the tissues. The compressed tissues become thinner while their healing is impeded. This may lead to a leak of the anastomosis before the tissues are healed. On the other hand, applying a light pressure may be inadequate to join the organs in a fluid tight manner, which can manifest with an immediate leak of the anastomosis.

Because of the significant risk of serious complications, none of these rigid connectors has found practical utilization. In addition, the walls of at least one of the two anastomosed organs must be flanged or cuffed. As it was explained above, this alone is a major limitation for the practical application of the connectors.

The present invention solves all these problems. It provides a new connector and methods for attaching the connector to hollow anatomical organs in an easy, fast, and reliable manner, which is overall superior to the currently used devices and methods for anastomosing and to these known of the prior art. The new connector has a wide and universal application. It can be used to perform end-to-end or side-to-end anastomoses of different hollow structures. It can be used for anastomoses of hollow body organs, for bypass and shunt procedures, for implantation of hollow artificial devices, for organ transplants, for intestinal stomas, and for other surgical procedures.

OBJECTS AND SUMMARY

It is a primary object of this invention to provide connectors for anastomosing a hollow anatomical structure with another hollow structure.

It is another object to provide a method for anastomosing a hollow anatomical structure with another hollow structure by connectors.

It is a further object to provide connectors that are simple to manufacture, easy to use, and cost-effective to implement.

These objects, and others are achieved in a connector comprising an annular rigid body and multiple holding members. The inner surface of the annular body conforms to the external surface around a wall-opening of a hollow anatomical structure. Holding means are affixed to the annular body. They holding means press the anatomical organ towards the annular body on the outside and keep the organ adjoined to the inner fluidproof surface of the rigid body. Embodiments for attachment to end-openings or to side-openings of anatomical organs are provided. The union of the annular body with another annular body of another connector attached to another hollow structure forms a fluidproof surface that surrounds the abutted cut-edges of the two approximated hollow structures.

Various modifications in the form and the structure of the connectors in accordance with the specific tissue and organ requirements are described. An additional instrumentation that facilitates the surgical implementation of the connectors is further provided. The implementation of the connector for new types of surgical procedures is shown.

A better understanding of the present invention along with its many attendant objects and advantages, may be obtained from consideration of the following description of the preferred specific embodiments, particularly when read in conjunction with the appended drawings, a brief description of which follows:

DESCRIPTION OF THE PREFERRED EMBODIMENTS

According to the present invention, I have developed a connector for attachment to hollow anatomical structures in a sufficiently fast, easy and reliable manner.

A specific preferred embodiment of an end connector and a method for attaching the connector to an end of a hollow tubular organ are shown in FIGS. 1A through 4C. For better visualization and understanding, the elements are shown in different views. They are shown in perspective views in FIGS. A. The same elements crosscut in half are shown in the same perspective views in FIGS. B. Portions of them, as defined by windows C* in FIGS. B, are shown magnified in schematic views in FIGS. C. Performing an end-to-end anastomosis of two hollow tubular organs attached with end connectors is shown in perspective views in FIGS. 5 through 7A. The end-to-end anastomosis crosscut in half is shown in a perspective view in FIG. 7B.

Figure 1A:
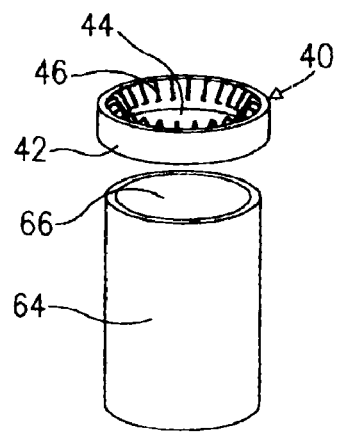
FIGS. 1A, 1B and 1C illustrate an end connector positioned above a hollow tubular organ. They are shown in a perspective view in FIG. 1A. The same connector and organ crosscut in half are shown in a perspective view in FIG. 1B. A portion of them (encircled by window C* in FIG. 1B) is shown magnified in a schematic front view in FIG. 1C.
Figure 1B:
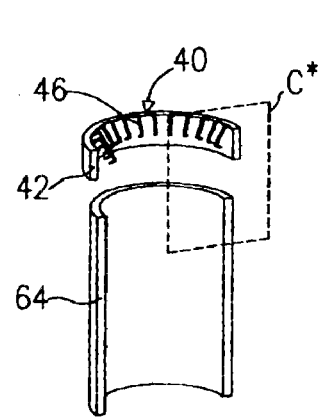
Figure 1C:
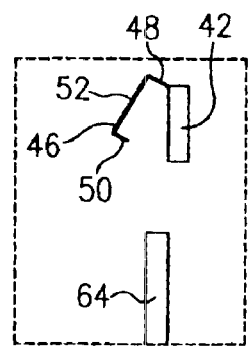

An end connector 40 is shown above an end-opening 66 of a hollow tubular organ 64 in FIGS. 1A, 1B and 1C. The connector 40 has an annular rigid body 42 and multiple holding members 46. The annular body is made of a material that is substantially rigid to sustain a stable coupling shape, such as a metal, a metal alloy, a hard plastic, or any other material with alike properties. The inner surface of the annular body has a predefined form that conforms to the external surface of the anatomical organ. In this case, the connector has an inner cylindrical surface that corresponds to the external cylindrical surface of the hollow organ. The opening 44 of the annular body 42 approximates the opening 66 of the hollow organ 64. The holding members 46 are made of a substantially rigid material that by an applied force can be deformed from one memory resident form to another memory resident form. Such a material can be made of various types of metal or metal alloy, such as stainless steel, or any other substance with like properties. The holding members 46 have a "U" shaped staple-like form consisting of first and second pointed ends 48 and 50 that are interconnected with a crossbar 52. With the first pointed ends 48, the holding members are affixed to the annular body 42 spaced apart along its opening 44.

Figure 2A:
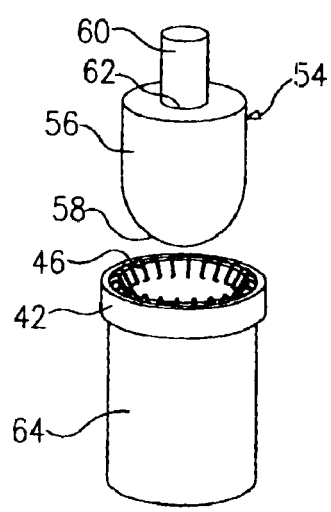
FIGS. 2A, 2B, and 2C illustrate the connector positioned over the end of the hollow organ and a pusher above them. They are illustrated in the same views as in FIGS. 1A, 1B, and 1C respectively.
Figure 2B:
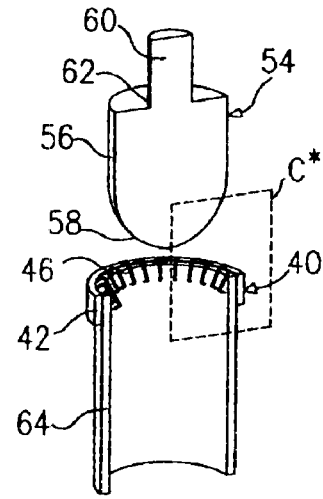
Figure 2C:
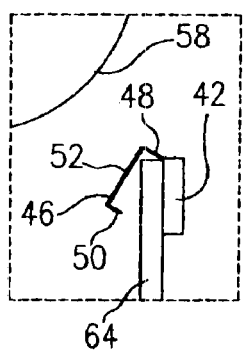

Attaching the connector to the end of the hollow organ is illustrated in FIGS. 2A through 4C. The connector 40 is positioned over the opening 66 of the hollow organ 64, as shown in FIGS. 2A through 2C. A pusher 54 is shown positioned above them. The pusher acts to deform the holding members. The pusher is made of a substantially hard material such as a metal, a metal alloy or of any other substance with alike properties. It has an approximately cylindrical body 56 affixed to the front end 62 of a rigid rod 60. The cylindrical body 56 has a dome-like front end 58.

The external diameter of the cylindrical body of the pusher approximates the internal diameter of the hollow organ.

Figure 3A:
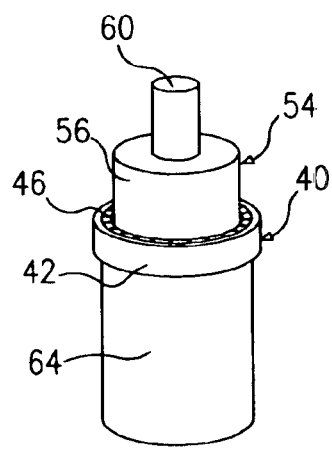
FIGS. 3A, 3B and 3C illustrate the holding members being deformed by the pusher inserted into the hollow organ. They are illustrated again in the same views as in the previous figures.
Figure 3B:
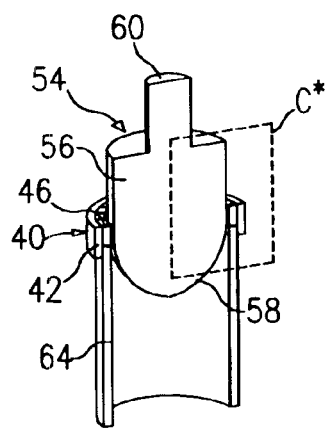
Figure 3C:
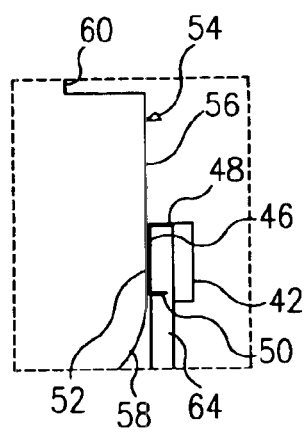
Figure 4A:
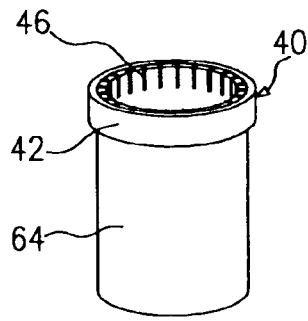
FIGS. 4A, 4B and 4C illustrate the connector attached to the end-opening of the hollow organ. They are illustrated again in the same views as in the previous figures.
Figure 4B:
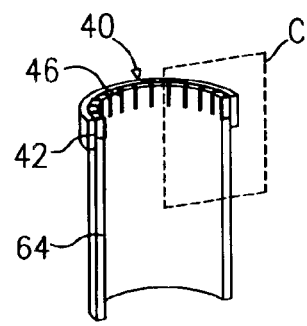
Figure 4C:
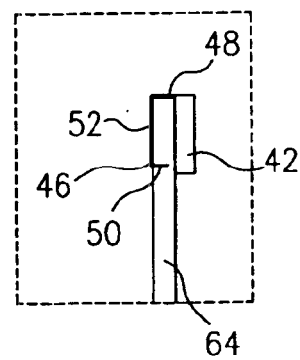
Figure 5:
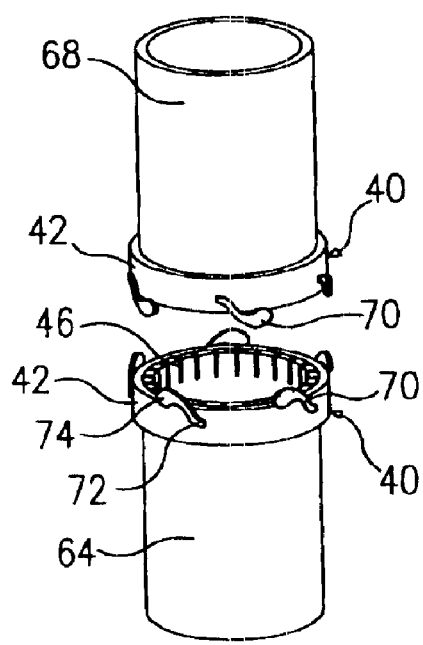
FIGS. 5, 6, and 7A illustrate in perspective views accomplishing an end-to-end anastomosis of two hollow tubular organs by a union of the connectors attached to their ends. The connectors are further provided with coupling arms.

Permanent attachment of the connector to the hollow organ is accomplished by deforming the holding members. This is illustrated in FIGS. 3A through 3C. By an applied force, the pusher 54 is moved axially downward into the opening 44 of the connector 40. The front end 58 of the pusher 54 exerts gradually increasing pressure on the holding members 46. This pushes and deforms the holding members in axial direction downward and in radial direction outward them. The holding members 46 bend along the points of attachment to the annular body 42. The deformed holding members 46 protrude into the opening 66 of the hollow organ 64. The crossbars 52 of the deformed holding members press from inside the wall of the hollow organ 64 towards the outside annular rigid body 42 of the connector 40. The second pointed ends 50 of the deformed holding members 46 pierce perpendicularly the wall of the hollow organ 64, which anchors the connector to the wall of the hollow organ. In this way, the connector becomes steadily attached to the opening of the hollow organ.

Figure 6:
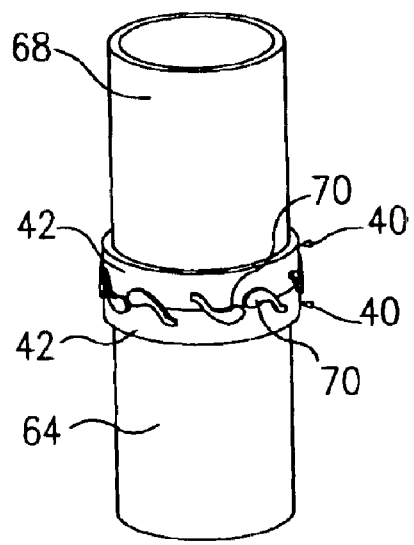
Figure 7A:
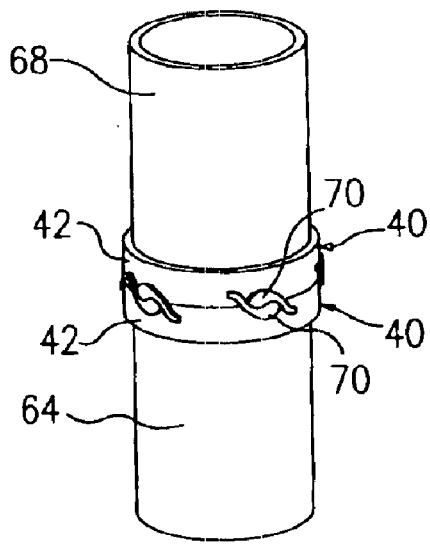

Performing an end-to-end anastomosis of two hollow tubular organs 64 and 68 attached with end connectors 40 is shown in a specific embodiment in FIGS. 5 through 7A. The end connectors comprise the same elements as described above—annular rigid bodies 42 and multiple holding members 46. The connectors are further equipped with means for coupling them. Multiple coupling arms 70 are attached with their first ends 72 to the outer surfaces of the annular bodies 42. The second ends 74 of the arms 70 have a predefined bud-like shape. The two organs 64 and 68 attached with connectors 40 and are shown close to each other in FIG. 5. To join the organs, the connectors 40 are first brought together, as shown in FIG. 6. After that the connectors 40 are rotated in opposite direction until the second ends 74 of their coupling arms 70 interlock into a permanent and stable position, as shown in FIG. 7A.

The union of two coupled connectors forms a fluidproof surface that surrounds the ends of the two organs being approximated and abutted with the cut-edges of their wall-openings. This precludes any possibility for a leak between their abutted edges. In this way, the two hollow organs attached with end connectors are anastomosed quickly, easily and reliably.

Figure 7B:
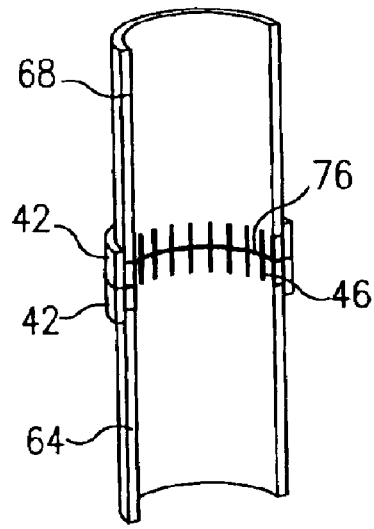
FIG. 7B illustrates in a perspective view the end-to-end anastomosis accomplished by a union of the end connectors, showing the anastomosis crosscut in half.
Figure 8A:
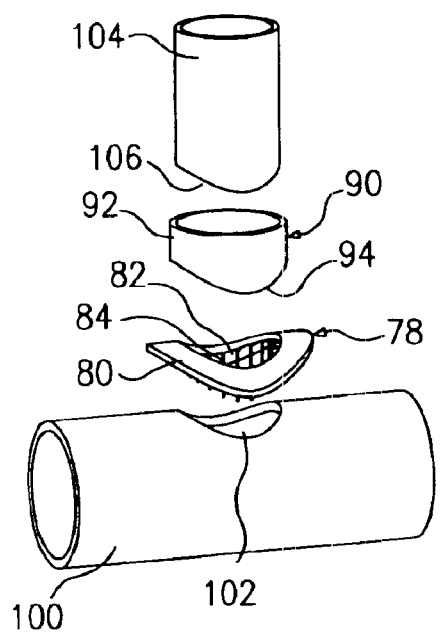
FIGS. 8A and 8B illustrate an end connector and a side connector positioned adjacent to the end and side-openings of two hollow tubular organs. The elements are shown in a side-front-top perspective view in FIG. 8A and crosscut in half in a side-front-bottom perspective view in FIG. 8B.
Figure 8B:
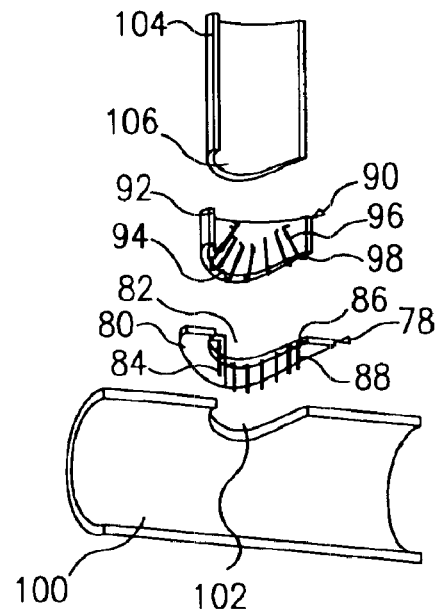
Figure 9A:
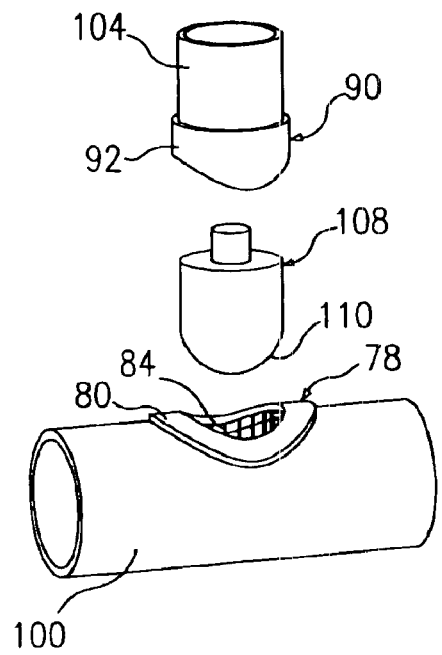
FIGS. 9A and 9B illustrate the two connectors positioned over the two hollow organs and a pusher directed perpendicularly to the side connector. They are shown in the same views as in FIG. 8A and 8B.
Figure 9B:
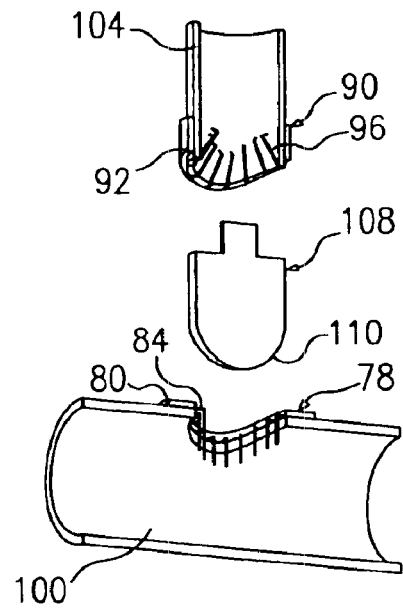
Figure 10A:
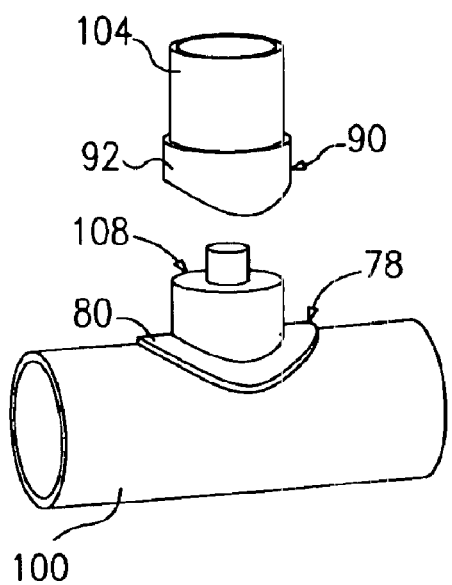
FIGS. 10A and 10B illustrate the pusher deforming the holding members of the side connector, showing them in the same views as in the previous figures.
Figure 10B:
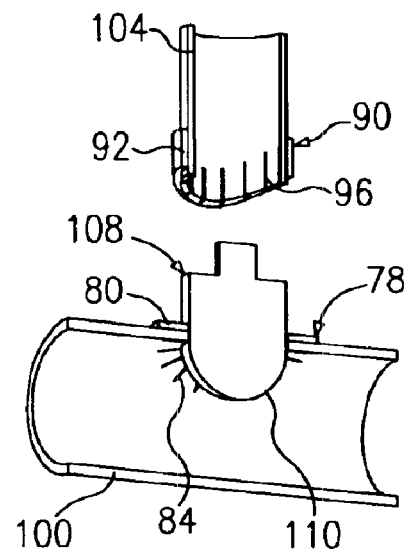

The end-to-end anastomosis of two hollow organs accomplished by connectors is seen best in FIG. 7B. This is an inside perspective view of the anastomosis, which is shown crosscut in half. As seen, the two organs 64 and 68 are exactly approximated with a minimal gap 76 between them. The size of the gap corresponds to the thickness of the holding members 46.

The circular staplers used currently for performing anastomoses of large gastrointestinal organs operate with staples made of wire with a diameter of approximately 0.01 mm. Wire with the same diameter can be used to produce the holding members of connectors for gastrointestinal organs. Then the gap, formed between the two gastrointestinal organs anastomosed by connectors, will also be 0.01 mm. Therefore, the gap is very narrow even for relatively large body organs. Accordingly, the gap is smaller for smaller body organs.

The narrow gap is quickly filled by the opposing edges of the two organs. Cutting body organs constitutes a trauma to their walls. The traumatized tissues are infiltrated quickly within the first hours and remain swollen for the next 36–48 hours. In this period, the swollen cut-edges of the two organs protrude between the holding members. The infiltrated tissues fill the small gap and the cut-edges contact with each other which actually eliminates the gap.

As seen, the two organs are exactly approximated and abutted with the cut-edges of their wall-openings. The internal, the medial, and the external layers of each of the two organs oppose and meet precisely with the same layers of the other organ. This leads to a fast and reliable healing that is a layer specific. A layer specific healing means that the internal, the medial, and the external layers of the two organs heal and join with each other. Such type of healing cannot be achieved with the current anastomotic devices. In majority of the current methods, the walls of the anastomosed organs are either inverted (gastrointestinal organs) or everted (blood vessels) and organs become joined by heeling of their external or internal layers only. Some current devices join organs by overlapping their walls. This positions in healing contact different layers, which leads to slow and weak healing.

A side connector for attachment to a side-opening of a hollow tubular organ and a method for performing a side-to-end anastomosis are described next in a specific preferred embodiment. Attachment of a side connector 78 to a first hollow tubular organ 100 and an end connector 90 to a second hollow tubular organ 104 is shown in FIGS. 8A through 11B. The elements are shown whole in perspective views in figures "A". The same elements are shown crosscut in half in perspective views from a lower point of view in figures "B". Accomplishing a side-to-end anastomosis of the two organs by the union of connectors attached to them is shown in FIGS. 12 through 14B.

The side connector 78 is based on the same principle as described above with the end connector. It has an annular rigid body 80 and multiple holding members 84. The annular body is made of a material that is substantially rigid to sustain a stable coupling form, such as a metal, a metal alloy, a hard plastic, or any other material with alike properties. The inner surface of the annular body has a predefined form that conforms to the external surface of the anatomical organ. In this case, the inner surface of the annular body corresponds reciprocally to the external surface of the side-wall of the first hollow organ. The opening 82 of the annular body 80 corresponds to the side-opening 102 of the first hollow organ 100.

The holding members 84 of the side connector 78 also follow the principles described above with the end-connector. They are made of a substantially rigid material that by an applied force can be deformed from one memory resident form to another memory resident form. The holding members have a "L" shaped form. They consist of shorter first arms 86 and longer second arms 88. With their first arms 86, the holding members 84 are affixed to the annular body 80 spaced apart along its opening 82.

The end-connector 90 of this embodiment also has an annular rigid body 92 and multiple holding members 96. The form of the annular body 92 and its opening 94 correspond respectively to the form of the second hollow organ 104 and its end-opening 106. The end-opening 106 of the second hollow organ 100 matches the side-opening 102 of the first hollow organ 100. The multiple holding members 96 of the end connector 90 resemble the "U" shaped holding members of the end connector described above for end-to-end anastomosis. They are with staple-like configuration, they are positioned spaced apart along the opening of the connector and directed towards the lumen of the hollow organ. In addition, the holding members 96 have short arms 98 by which they are attached to the annular body 92 of the connector 90, as seen in the crosscut views in FIGS. 8B and 9B. These short arms extend the holding members 96 axially and downward. This extension equals to the thickness of the annular body 80 of the side connector 78. In this way, when the two connectors 78 and 90 are coupled, the end of the second hollow organ 104 protrudes downward and contacts the wall of the first hollow organ 100.

Figure 11A:
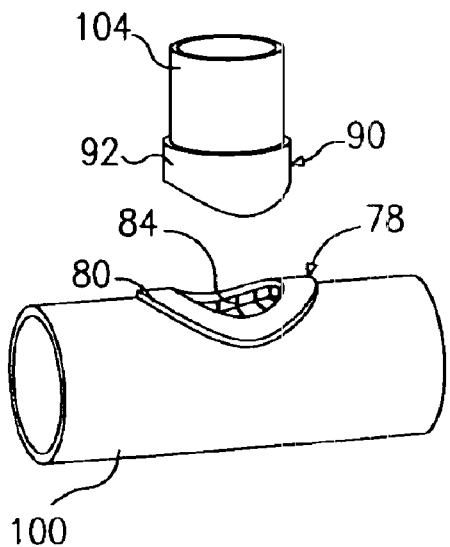
FIGS. 11A and 11B illustrate the end connector and the side connector attached to the two hollow tubular organs, showing them in the same views as in the previous figures.
Figure 11B:
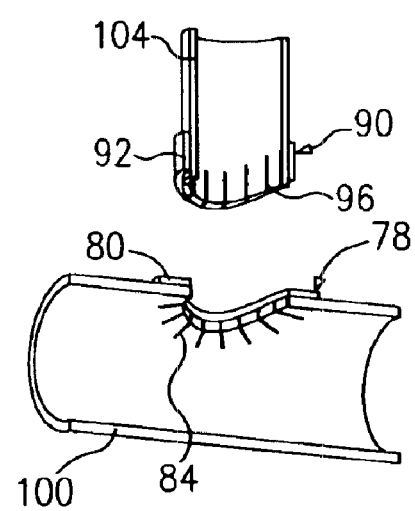
Figure 12:
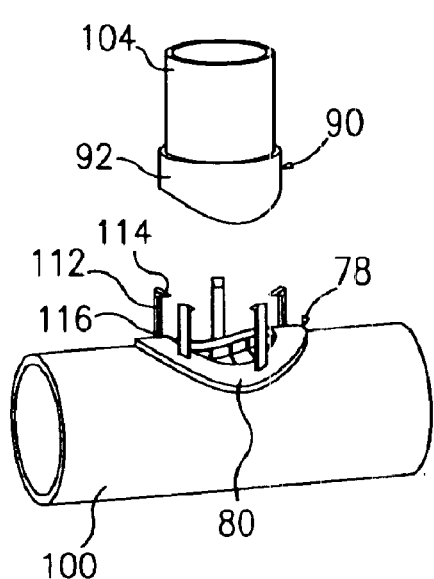
FIGS. 12, 13, and 14A illustrate performing a side-to-end anastomosis of two hollow tubular organs by a union of the connectors attached to them, showing them in side-front-top views. The connectors are further provided with coupling arms.
Figure 13:
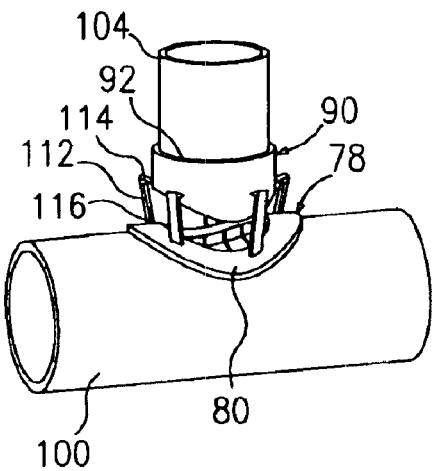

Deforming the holding members 84 of the side connector is accomplished by a pusher 108, which is shown in FIGS. 9A through 10B. It is performed in the same manner as described above with end-to-end connectors. The pusher 108 is moved down into to the opening 82 of the side connector 78. The dome front end 110 of the pusher 108 exerts gradually increasing pressure axially downward and radially outward on the holding members 84. The holding members 84 bend along the point of attachment to the annular body 80 into the side-opening 102 of the first hollow organ 100. The second arms 88 of the deformed holding members 84 press the wall of the first hollow organ 100 from the inside towards the annular rigid body 80 on the outside. In this way, the side connector is attached steadily to the sidewall of the first hollow organ. The holding members 96 of the end connector 90 are deformed in the same way as depicted above with end-to-end connectors, so this is not described again. The two connectors 78 and 90 attached to the two hollow organs 100 and 104 are shown in FIGS. 11A and 11B.

A side-to-end anastomosis of the two organs 100 and 104 is performed by coupling the two connectors 78 and 90 attached to them in a fluidproof union, which is shown in a specific preferred embodiment in FIGS. 12 through 14B. The connectors are further equipped with means for coupling them. Multiple locking arms 112 are affixed with their first ends 114 to the outer surface of the annular rigid body 80 of the side connector 78. They are positioned perpendicular and spaced apart so they can accept the annular body 92 of the end connector 90. The second ends 116 of the locking arms 112 are curved inwardly in a hook-like form.

Anastomosis of the two organs 100 and 104 is accomplished by bringing together the connectors 78 and 90 attached to them. The locking arms 112 of the side connector 78 encompass and lock by their second ends 116 the annular body 92 of the end connector 90. The union of the two coupled connectors forms a fluidproof surface that surrounds the cut-edges of the two approximated organs, which securely precludes leaks out of the anastomosis. In this way, the two organs are anastomosed easily and reliably.

Figure 14A:
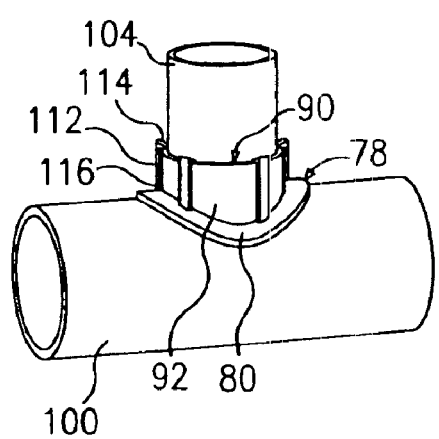
Figure 14B:
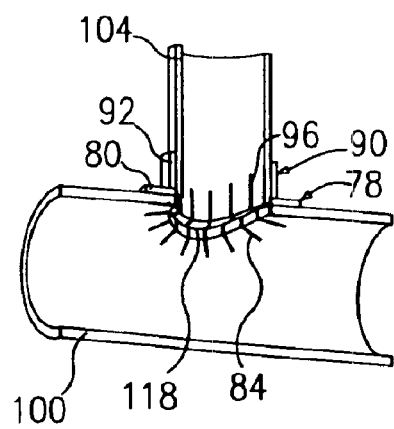
FIG. 14B illustrates in a perspective view the side-to-end anastomosis accomplished by a union of the attached connectors, showing the anastomosis crosscut in half.

The side-to-end anastomosis of the two organs is seen best in inside view in FIG. 14B. As seen, the two organs 100 and 104 are precisely approximated and abutted with cut-edges of their openings, which are closely adjacent to each other with a minimal gap 118 between them. The union of the two annular bodies forms a fluidproof surface that surrounds the cut-edges of the two organs and prevents leaks out of the anastomosis. This warrants fast and reliable healing of the two organs.

The connector of the present invention can be used for variety of purposes with different body organs and artificial structures. They can be used with arteries, veins, small or large bowels, stomach, bile duct, ureter, and other hollow body organs such as the skull, thorax or abdomen. They can be also used with artificial grafts or organs, such as vessel grafts or total artificial hearts, for replacing the natural body structures and organs. All these organs and structures differ physiologically, anatomically, and functionally. Their walls may be rather thick (stomach), or thin (veins). The pressure inside them may be very high (arteries), or low (intestines). They may conduct different types of fluids that are erosive (urine), or not erosive (blood). They may contain secreting glands in their walls (gastrointestinal organs), or have no glands (blood vessels). Their regenerative and healing capacities may be fast (intestines), or slow (ureters).

Without departing from the principles of the present invention described above, various modifications in the form and the structure of the connectors can be made easily in order to comply with the specific needs of the different anatomical structures. Several such modifications are shown next.

Figure 15:
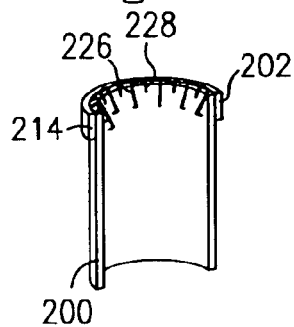
FIGS. 15, 16, 17 illustrate in perspective views three different embodiments of end connectors with different holding members, showing the embodiments crosscut in half.
Figure 16:
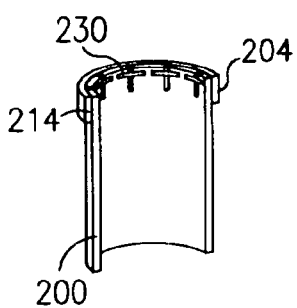
Figure 17:
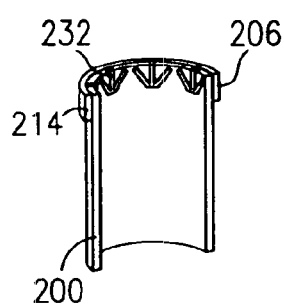

Three specific embodiments of end connectors with modified holding members are shown crosscut in half in perspective views in FIG. 15, FIG. 16 and FIG. 17. In the first embodiment of FIG. 15, the holding members are a combination of "U" shaped members 226 and "L" shaped members 228 affixed to the annular rigid body 214. The "L" shaped members are shorter than the "U" shaped members. The connector 202 is anchored to the hollow organ 200 by the pointed ends of the "U" shaped holding members 226. The "L" shaped holding members 228 only press the wall of the organ near the end. In this way, the wall of the hollow organ remains well pressed to the annular body of the connector, while it is punctured only by half of the holding members. This decreases the risk of rupture of the hollow organ in the puncture line. Such embodiment can find useful application for organs that have fragile walls and do not conduct fluid under high pressure (e.g., veins and intestines).

Two other embodiments of connectors 204 and 206 with different type of holding members are shown in FIGS. 16 and 17. The holding members 230 have a cross shape in the first embodiment 204 in FIG. 16, and an arrow shape 232 in the second embodiment 206 of FIG. 17. In both cases, the number of the holding members is reduced and each of the members presses the hollow organ 200 on a larger surface. Such embodiments may find application for organs with thick walls and/or slow regenerative capacities (e.g., stomach or ureters).

Figure 18A:
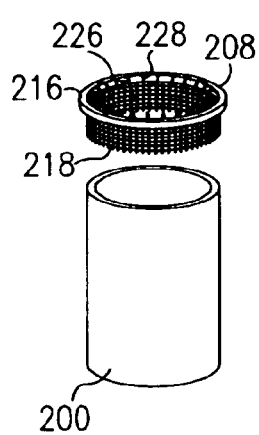
FIGS. 18A and 18B illustrate in perspective views a different embodiment of an end connector with an annular body comprising a wire mesh.
Figure 18B:
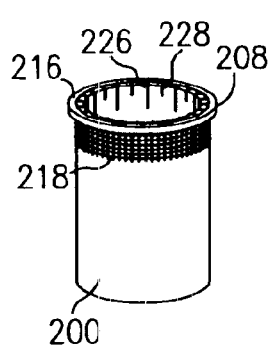

The annular rigid body of the connector can also be modified, as illustrated next. A specific embodiment of an end connector 208 is shown adjacent and attached to the end of a hollow body organ 200 in FIGS. 18A and 18B respectively. In this case, the connector consists of a narrow rigid ring 216 and a wire mesh ring 218 below it. This embodiment has two distinctive features. First, the mass and accordingly the weight of the connector are reduced. Second, a connective tissue from the external layer of the body organ can grow into the wire ring and produce a natural attachment of the connector to the body organ.

Figure 19A:
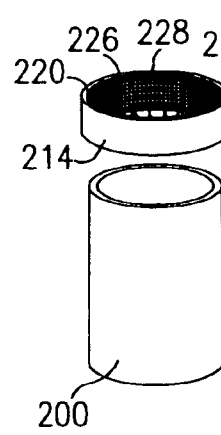
FIGS. 19A and 19B illustrate in perspective views a different embodiment of an end connector comprising an annular body lined internally with a layer of fabric.
Figure 19B:
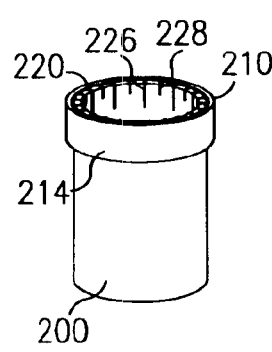

Another specific embodiment of an external end connector 210 with a modified annular body is shown in FIGS. 19A and 19B. The rigid annular body 214 is lined on the inside with a thin layer of fabric 220 that is woven, knitted or braided. Such layer of fabric can be made of Dacron™, Teflon™, or others brands, which have already been proven biocompatible for vessel prostheses.

As the fabric 220 remains entirely outside the lumen of the hollow body organ 200, fabrics made of less biocompatible fibers can be used as well. In addition, the inner surface of the annular body of the connector can also be covered with any other substance that has a porous microstructure that allows the ingrowth of connective body tissue.

The connector lined internally with fabric material has two important features. First, the fabric material cushions the connector so the body organ is not pressed to a hard surface. Second, connective tissue fibers can grow from the external surface of the body organ into the porous structure of the fabric material. This produces natural healing and attachment of the connector to the body organ.

Figure 20A:
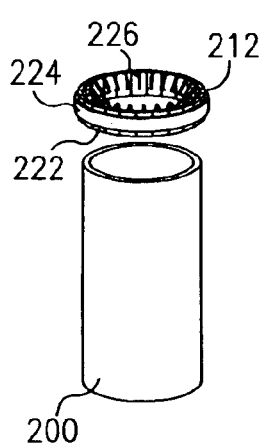
FIGS. 20A, 20B and 20C illustrate in perspective views a different embodiment of an end connector with an annular body comprising multiple arcuate segments bound by a bioabsorbable strip.
Figure 20B:
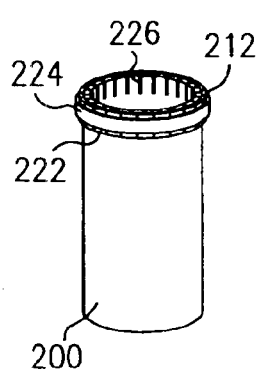
Figure 20C:
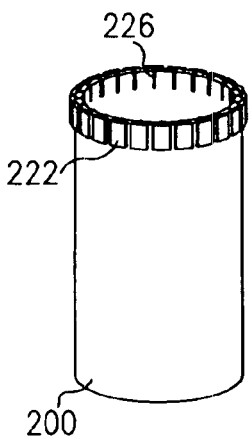

Another specific embodiment of an end connector with a modified annular rigid body is shown in perspective views FIGS. 20A, 20B, and 20C. The connector 212 is shown above the end of hollow body organ 200 in FIG. 20A and attached to it in FIG. 20B. The annular rigid body of the connector 212 is formed by multiple arcuate rigid segments 222 that are kept in a stable annular formation by an annular stripe 224. The annular stripe 224 is made of a bioabsorbable material that is absorbed by the body within two weeks to six months. During this period the anastomosed body organs have joined reliably by natural healing. Later, when the body organ 200 grows and enlarges, the arcuate segments 222 distance from each other, as shown in FIG. 20C. In this way, the connector does not restrict the physiological growth of the body organ. Such an embodiment can find particularly beneficial application in pediatric surgery.

A further simplification and improvement of this embodiment is to manufacture the entire annular body of the connector only of bioabsorbable material, when such a suitable material that is rigid enough to sustain a stable coupling shape proves to be available in practice. It is preferable to manufacture also the holding members from absorbable material, when such a material that is rigid and can be deformed from one memory resident form to another form becomes available.

Figure 21A:
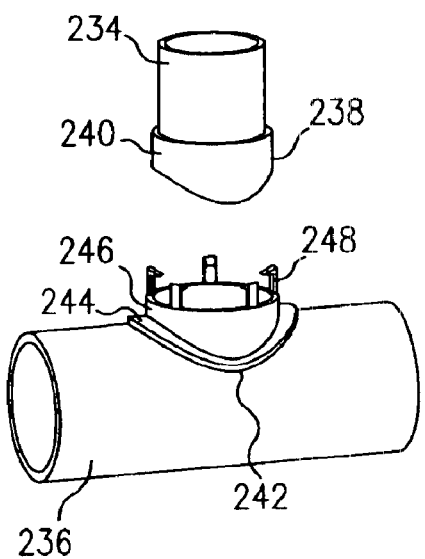
FIGS. 21A and 21B illustrate in perspective views a side-to-end anastomosis of two hollow organs accomplished by a union of connectors with different coupling configurations of their annular bodies.
Figure 21B:
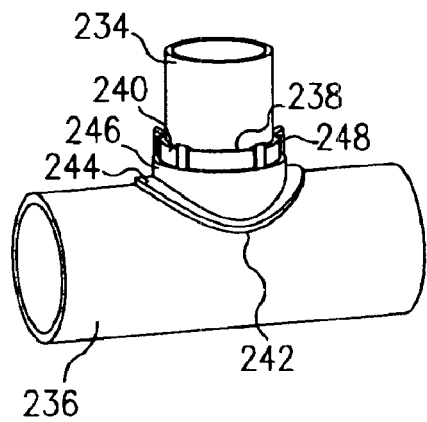

The connectors can be produced with various configurations for coupling. A side-to-end anastomosis of two organs 234 and 236 accomplished by specific embodiments of connectors 238 and 242 that plug into each other is shown in FIGS. 21A and 21B. In this case, the side connector 242 further comprises a cylindrical portion 246 affixed perpendicularly to the annular rigid body 244. The cylindrical portion 246 has predefined form and dimension to accept and encompass tightly the annular rigid body 240 of the end connector 238. The connectors are joined in stable position by multiple hook-like coupling arms 248 of the side connector 242, which lock around the annular body 240 of the end connector 238.

Figure 22A:
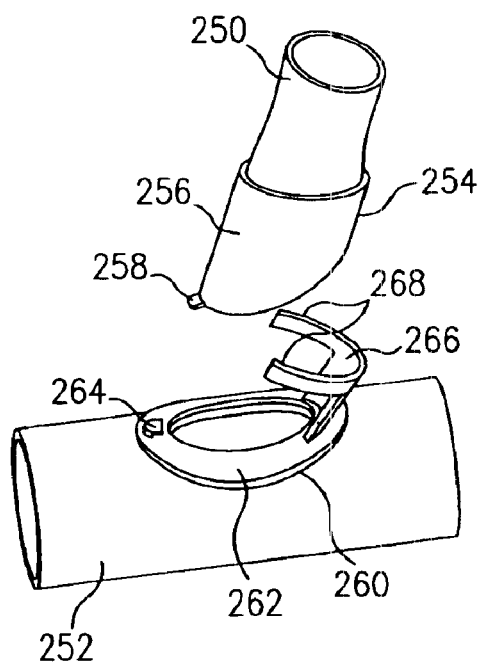
FIGS. 22A and 22B illustrate in perspective views a side-to-end anastomosis at acute angle of two hollow organs accomplished by a union of connectors with different means for coupling.
Figure 22B:
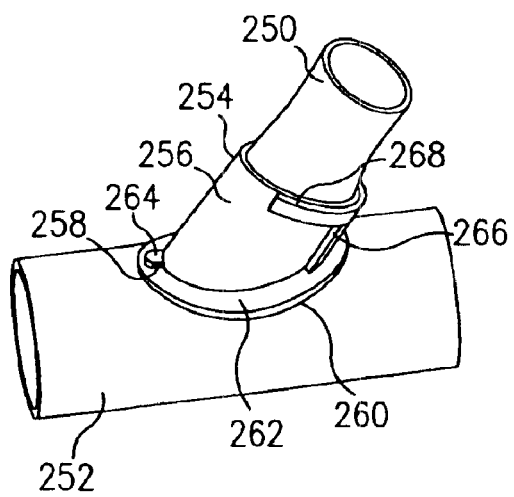

Another specific embodiment of connectors for accomplishing side-to-end anastomosis of two hollow tubular organs 250 and 252 is shown in FIGS. 22A and 22B. The end connector 254 is coupled to the side connector 260 at an acute angle. In this case, the illustrated connectors are coupled at angle of 60 degrees. The side-opening is not strictly cylindrical, but oval. In this way, the anastomosis is performed on a relatively flat surface. The two connectors 254 and 260 are coupled and locked in a stable position by a den 258 of the end connector that fits in a recess 264 of the side connector 260, and by an arm 266 of the side connector 260 which by two branches 268 braces the annular body 256 of the end connector 254.

Figure 23A:
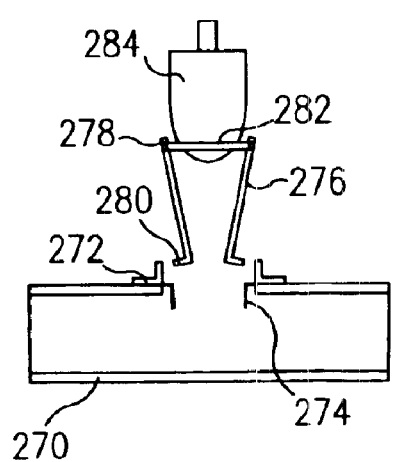
FIGS. 23A and 23B illustrate in schematic front views other means for deforming the holding members of a side connector.
Figure 23B:
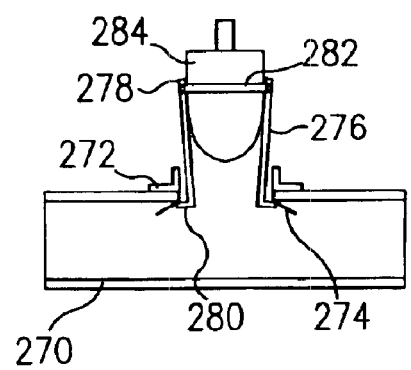

The holding members can be deformed by a variety of means and methods, some of which are described next. Other means for deforming the holding members 274 of a side connector 272 are shown schematically in FIGS. 23A and 23B. Multiple levers 276 are hinged with their first ends 278 to a rigid ring 282. With their second ends 280, the levers 276 abut the holding members 274. A pusher 284, with an approximately cylindrical body and a dome like front end, is positioned in a central axial orientation. By an applied force, the pusher 284 is moved axially down. This pushes the levers 276 radially and outwards. The levers 276 turn along their first ends 278. The second ends 280 of the levers 276 move in a radial direction outward, which deforms the holding members 274, which is illustrated in FIG. 23B.

Figure 24:
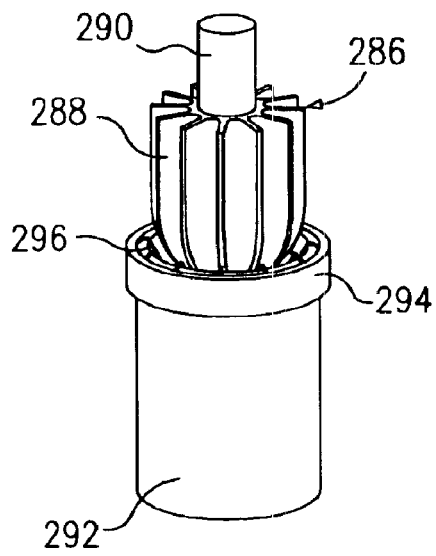
FIG. 24 illustrates in a perspective view other means for deforming the holding members of an end connector.

Other means for deforming the holding members 296 of an end connector 294 are shown in FIG. 24. In this embodiment, the pusher 286 consists of multiple rigid plates 288 arrayed radially over a cylinder 290. The plates 288 are inwardly curved so the front end of the pusher has overall a dome-like shape. When the pusher 286 is moved downward, the plates 288 exert pressure only on the holding members. In this way, the hollow organ 294 is not traumatized by the pusher 286.

Figure 25:
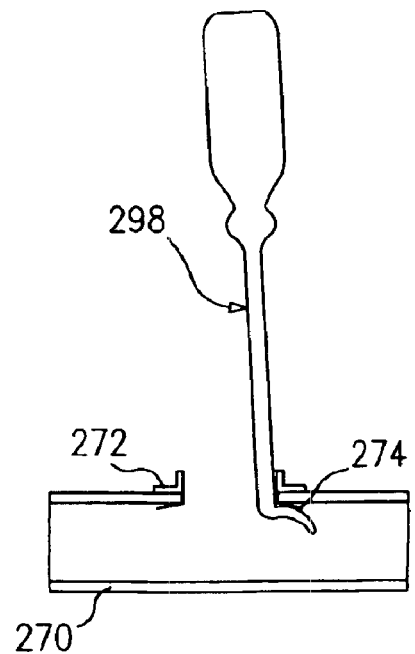
FIG. 25 illustrates in a schematic front view other means for checking and deforming the holding members of a side connector.

The holding members can be deformed also by very simple means. This is illustrated schematically in FIG. 25, which shows deforming the holding members of a side connector 272 attached to a hollow organ 270. The holding members are deformed one by one with an appropriately curved spatula 298, which is rotated and pulled up consecutively. This method can be used exclusively or in addition to the other shown and known methods. With the spatula, the surgeon can check the position of the holding members deformed by another method and to bend them additionally, if needed.

The methods described above are just exemplary illustrations for deforming holding members by externally applied forces and other known methods can be implemented for this purpose.

It should be noted that intrinsic elastic forces can also be used to deform the holding members. The holding members can be made by a highly elastic rigid material such as nickel and titanium alloy (nitinol) metal. In such cases the holding members are initially modeled in the desired deformed shape. Then, they are opened so they can accept the wall of the hollow organ. When released, they return back to their initial shape under their intrinsic elastic force.

Figure 26A:
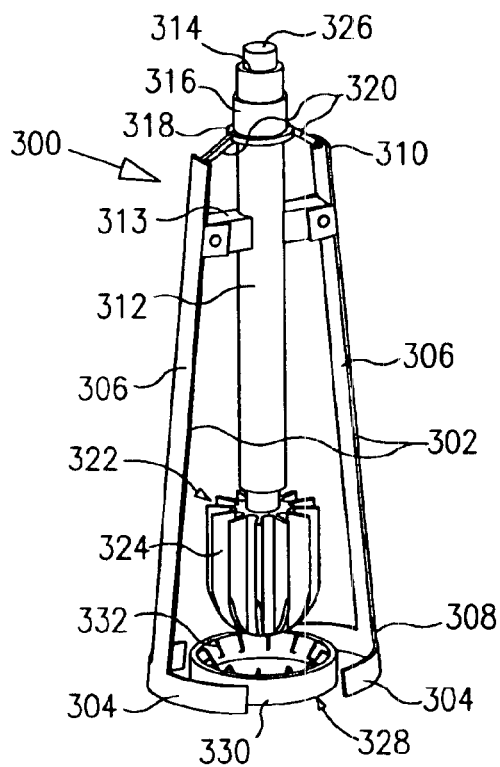
FIGS. 26A and 26B illustrate in perspective views a connector-holder used to hold and align an end connector with a pusher.
Figure 26B:
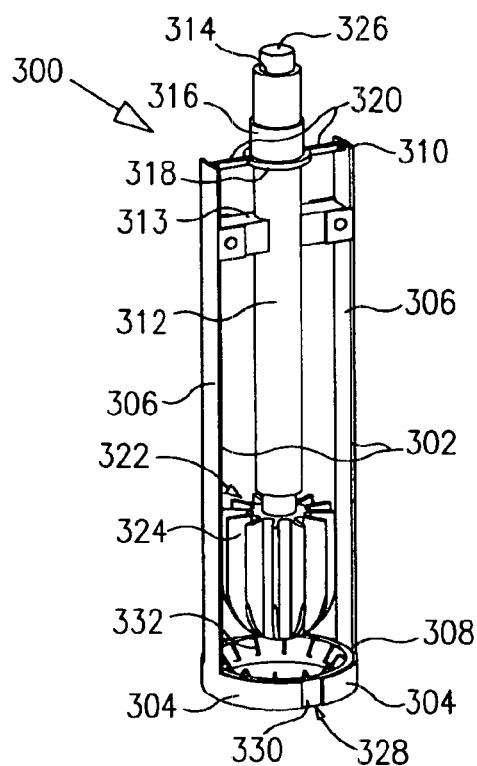
Figure 27A:
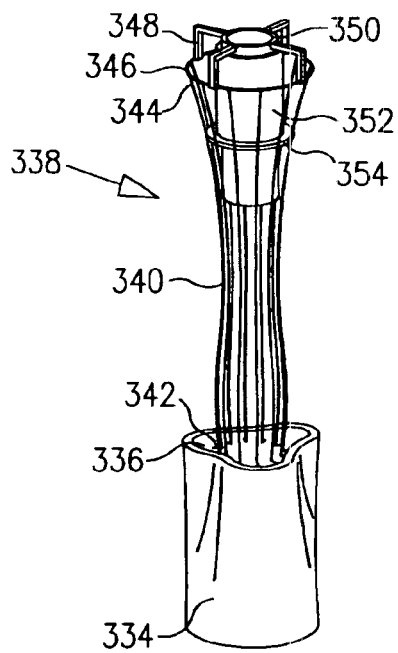
FIGS. 27A and 27B illustrate in perspective views an organ-holder used to hold and align the end of a hollow tubular organ.
Figure 27B:
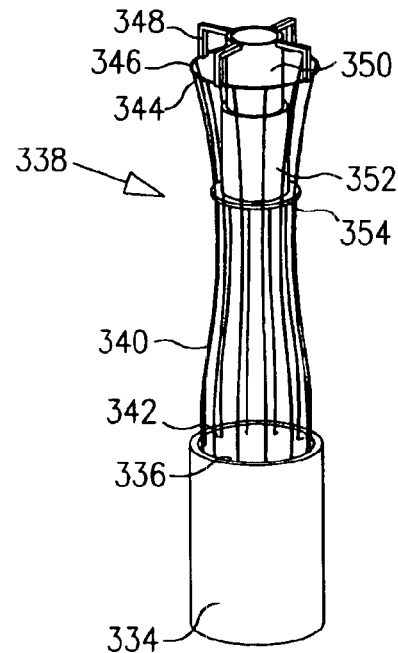
Figure 28:
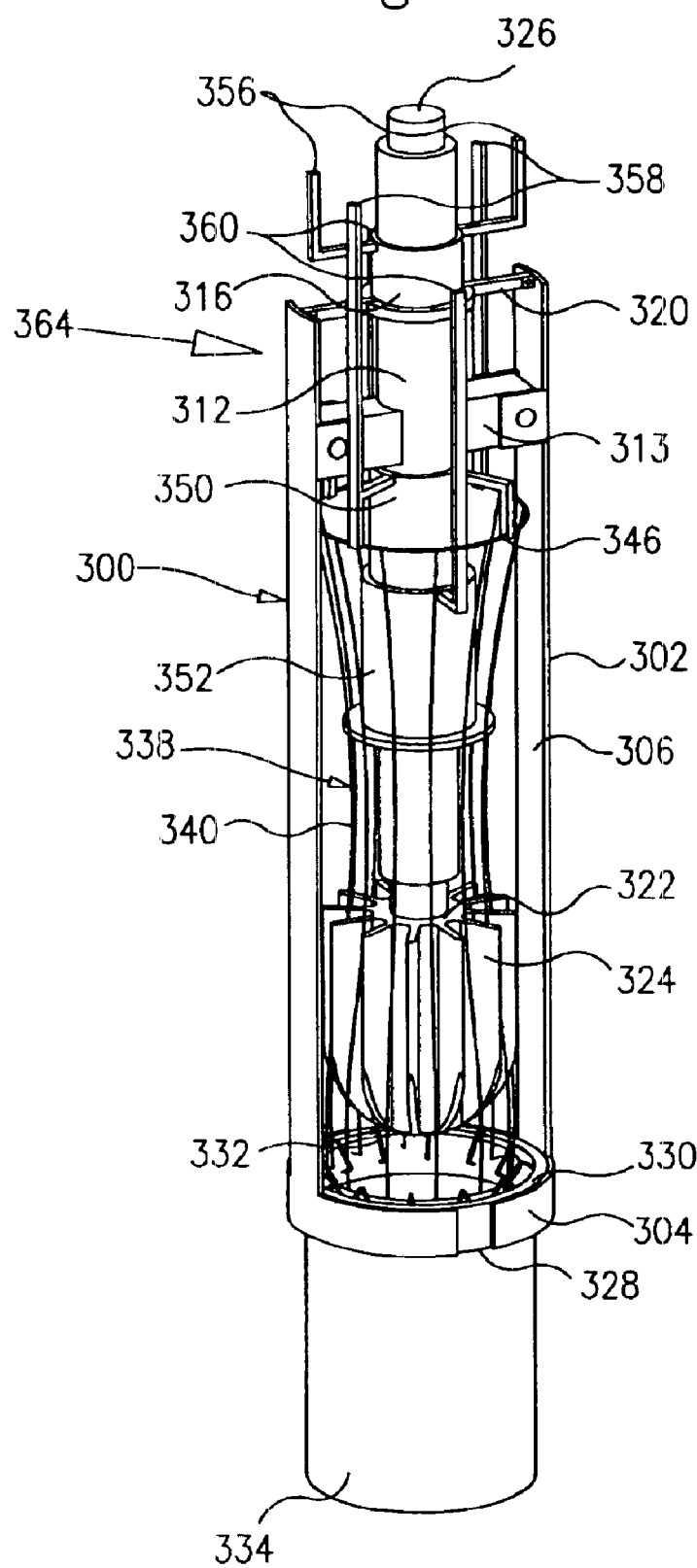
FIG. 28 illustrates in a perspective view the connector holder and the organ holder combined in a single front unit.
Figure 29:
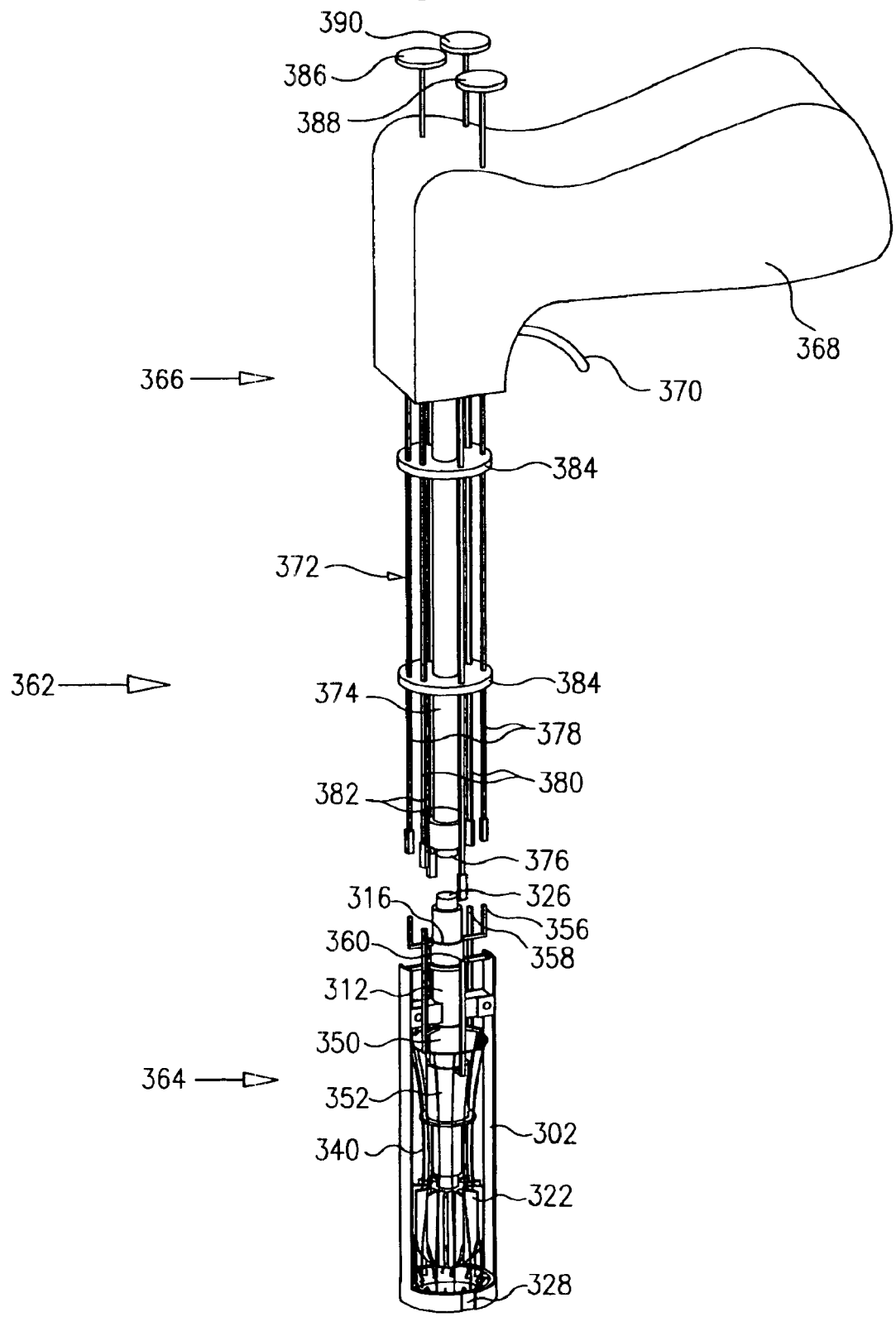
FIG. 29 illustrates in a perspective view a connector-applying instrument comprising a gun shaped body and a front unit.
Figure 30:
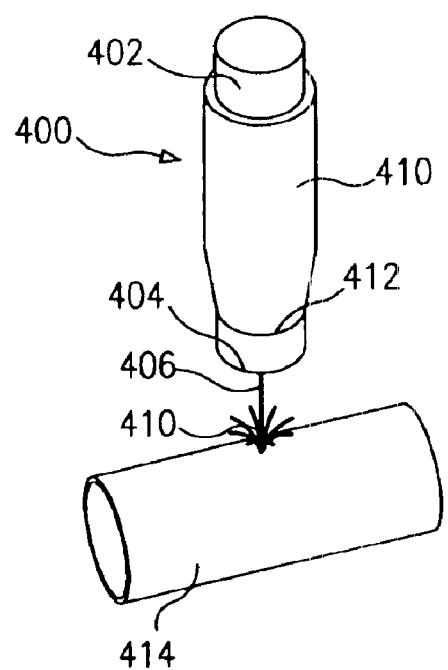
FIGS. 30 through 33 illustrate in perspective views a cutting instrument for performing a side-opening in a hollow organ.

The surgical procedure for attaching a connector to a hollow organ can be further automated and facilitated by additional instrumentation. An exemplary illustration of such instrumentation is a specific embodiment of a connector-applying mechanism shown next. For better visualization and understanding, the components of this mechanism are shown and described consecutively. First, an instrument that holds the connector, referred to as a connector holder 300, is shown in FIGS. 26A and 26B. After that, an instrument that holds the end of a hollow organ, referred to as an organ holder 338, is shown in FIGS. 27A and 27B. The connector holder and the organ holder combined in a single front unit 364, are shown in FIG. 28. The whole connector-applying mechanism 362 is illustrated in FIG. 29.

The connector holder 300, illustrated in FIGS. 26A and 26B, consists of a pair of pivoted jaws 302 attached to a central cylinder 312. The jaws 302 consist of semi circular arcuate portions 304 positioned at the lower ends 308 and of two long arms 306 extending upward. The arcuate portions 304 encompass tightly the annular body 330 of the connector 328 when the jaws are closed. The arms 306 are pivoted to two radial projections 313 of the central cylinder 312 at points closer to the upper ends 310 of the arms. A first sliding cylinder 316 that has a small radial flange 318 is slidingly positioned over the central cylinder 312. Two beveled levers 320 are joined pivotally with their ends to the upper ends 310 of the arms 306 and to the radial flange 318 of the first sliding cylinder 316. A pusher 320, consisting of multiple radial plates 324 is used to deform the holding members 332.

The rigid rod 326 of the pusher 320 extends axially upward through a bore 314 of the central cylinder 312.

When the first sliding cylinder 316 is moved down, the beveled levers 320 push the upper ends 310 of the arms 306 radially and outward. The arms 306 turn around their pivoting points with the radial projections 313 of the central cylinder 312. Their lower ends 308 move in inward radial direction. The arcuate portions 304 of the jaws 302 brace the annular body 330 of the connector 328 and hold it in a stable position. In this way, the connector 328 is oriented precisely with the axis of the pusher 322. Moving up the first sliding cylinder 316 opens the jaws and releases the connector 328 after the procedure is completed.

The organ holder 338 is illustrated in perspective views in FIGS. 27A and 27B. It keeps the end of a hollow organ 334 in a stable position during the attachment procedure. Multiple long wire pins 340 are used to hold the hollow organ 334. The wire pins 340 extend axially and are curved radially inwards. The lower ends 342 of the pins 340 are angled perpendicularly to the wall of the hollow organ 334. The upper ends 344 of the wire pins 340 are attached to a rigid ring 346. The ring 346 is attached by four "L" shaped supporting arms 348 to a basic cylinder 350. A second sliding cylinder 352 is slidingly positioned over the basic cylinder 350. The second cylinder 352 has an outward radial flange 354 in the lower end.

During the procedure, the basic cylinder 350 is moved down so the lower ends 342 of the pins 340 are positioned just below the edge of the hollow organ 334, which is illustrated in FIG. 27A. Then, the second sliding cylinder 352 is moved down, as shown in FIG. 27B. Its flange 352 pushes the wire pins 340 in an outward radial direction. The lower ends 342 of the pins 340 move outward radially. They pierce the wall of the hollow organ 334 and expand it to an exact cylindrical configuration. In this way, the hollow organ is held in a stable position mounted on the wire pins.

The connector holder 300 and the organ holder 338 are combined in a single front unit 364, which is shown in FIG. 28. The basic cylinder 350 of the organ holder 338 is slidingly positioned over the central cylinder 312 of the connector holder 300. In this way, the hollow organ 334, the connector 328, and the pusher 322 are all held in a stable position and aligned precisely with each other. Three pairs of axially extending bars 356, 358, and 360 are affixed accordingly to the first sliding cylinder 316, to the basic cylinder 350, and to the second sliding cylinder 352.

The connector-applying mechanism 362 is shown in FIG. 29. It consists of a gun shaped body 366 and the single front unit 364. The drawing illustrates in general the major components of the body of the connector-applying mechanism. It consists of a handle 368, a trigger 370, and an elongated tubular portion 372. The elongated portion 372 consists of axial extensions of the same components as of the front unit: an extension 374 of the central cylinder 312; an extension 376 of the rigid rod 326 of the pusher 322; and three pairs of extension 378, 380, and 382 of the three pairs of bars 356, 358, and 360 of the first sliding cylinder 316, the basic cylinder 350, and the second sliding cylinder 352 respectively. Two thin circular plates 384, affixed perpendicularly to the extension 374 of the central cylinder 312, sustain and direct the movement of the three pairs of extensions 378, 380, and 382 in an axial direction.

Each of the three pairs of extensions continues through the handle and ends with a button situated on the backside of the handle. The first button 386 is the end of the extension 378 of the pair of bars 356 affixed to the first sliding cylinder 316, which is coupled to the upper ends of the jaws 302. Pushing down the first button 386 moves down the first sliding cylinder 316, which closes the jaws 302 of the connector holder 300. The second button 388 is the end of the extension 380 of the pair of bars 358 of the basic cylinder 350, to which the multiple wire pins 340 are attached. Pushing down the second button 388 introduces the lower ends 342 of the wire pins 340 into the hollow organ 334. The third button 390 is an extension 382 of the pair of bars 360 affixed to the second sliding cylinder 352. Pushing down the third button 390 moves down the second sliding cylinder 352, which expands the wire pins 340 that keep the organ in a stable position.

The trigger 370 is coupled to the extension 376 of the rigid rod 326 of the pusher 322 by a trigger mechanism in a manner that pulling the trigger moves axially downward the extension of rigid rod. In this way, pulling the trigger 370 moves down the pusher 322, which deforms the holding members 322 of the connector 328. The trigger mechanism can be executed in many already known from prior art methods, one of which was shown in the parent patent application, and this is not described here in details.

The surgeon attaches the end connector 328 to the opening 336 of the hollow organ 334 by the connector-applying mechanism 362 in an quick and easy way. First, the connector-applying mechanism 362 is assembled. The surgeon selects a connector 328 and a front unit 364 with appropriate sizes that correspond to the dimensions of the hollow organ 334. Then, the surgeon couples the front unit 364 to elongated portion 372 of the gun shaped body 366. By pushing the first button 386 down, the jaws 302 of the connector holder 300 grasp the connector 328 in stable position. It should be noted that front units with different sizes (and accordingly connectors) can be coupled to a same gun shaped body. This improves the cost effectiveness of the connector-applying mechanism.

After the connector-applying mechanism 362 is assembled, the surgeon begins the actual attachment of the connector 328 to the hollow organ 334. First, the second button is pushed down which introduces the pins 340 into the hollow organ 334. Then, the surgeon pushes down the third button 390, which expands the pins 340 and secures the organ 334 in a stable position. After that the surgeon pulls up the second button 388, which aligns the end of the mounted organ 334 with the connector 328. At this moment, the trigger 370 is pushed. This moves down the pusher 322 and deforms the holding members 332. In this way, the connector 328 becomes attached to the hollow organ 334. After that, by pulling up the third 390 and the first button 286, which respectively collapse the wire pins 340 and open the jaws 302, the connector-applying mechanism 362 is released and removed away.

Using the connector-applying mechanism, the surgeon can attach the connector from a distance only with one hand. This allows the connector to be attached in minimally invasive procedures under endoscopic control. For application with relatively large body organs (such as intestines), the connector-applying mechanism can be modified further. An endoscopic apparatus can be introduced through a bore of the rigid rod of the pusher. This will provide the surgeon with a good central view of the organ and the connector during the procedure.

The connector-applying mechanism was described above in general. Minor details that are obvious to one skilled in the art were not shown. For example, by matching ridges and grooves, the pusher and the connector can by aligned so the radial plates of the pusher are aligned with the holding members of the connector. In the same way, the basic, first and second sliding cylinders can be directed to move strictly axially without any rotation. Also, springs and other means can be used to keep the moving elements in a basic position.

The connector-applying mechanism shown above should be considered a basic exemplary illustration of such a mechanism. Many modifications in its structure can be made by one skilled in the art. In a similar manner, a connector-applying mechanism for attaching a side connector can be constructed.

An exact matching of the openings of the connector and the hollow organ is needed in order to attach the connector easily and reliably. A side-opening of a hollow tubular organ is rather difficult to perform as the side-opening has a rather complex configuration that is formed by the intersection of two cylindrical organs.

A cutting instrument 400 that creates easily and precisely a side-opening in a hollow tubular organ 414 is shown next in FIGS. 30 through 33. The cutting instrument comprises a basic rigid rod 402 and a cutting cylinder 410 positioned slidingly over the rod. The cutting cylinder has a sharp lower edge 412. A thin shaft 406 is affixed axially to the lower end 404 of the basic rod 400. The shaft 406 ends up with a pointed barbed end 408.

Figure 31:
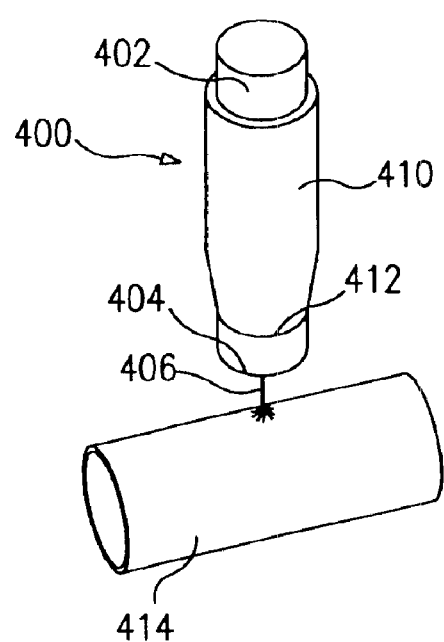
Figure 32:
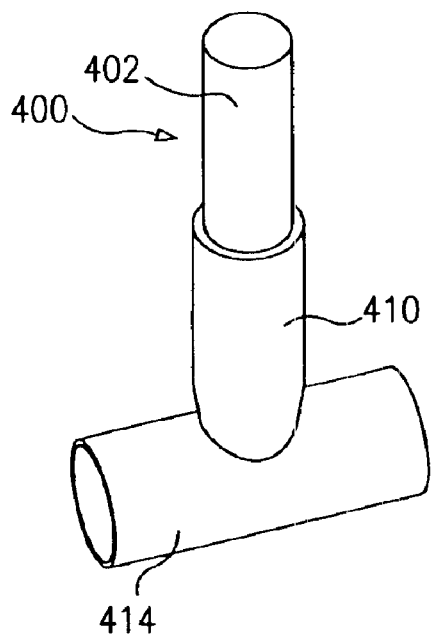
Figure 33:
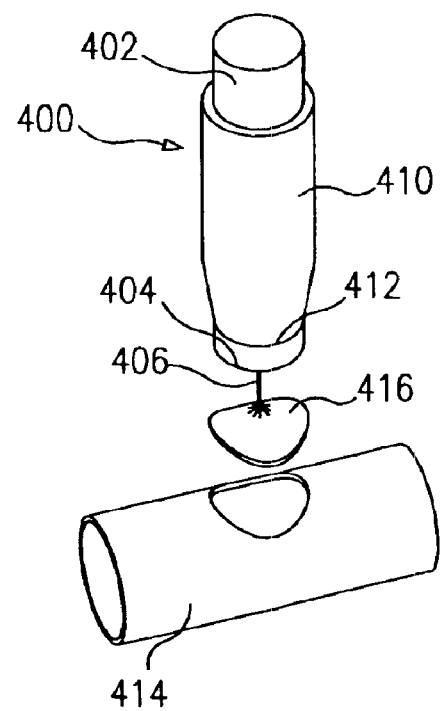

Cutting the sidewall of the hollow organ is shown in different phases in FIGS. 31 through 33. First, the cutting instrument 400 is pushed down so the barbed end 408 of the shaft pierce the wall of the organ 414, as shown in FIG. 31. Then, the cutting cylinder 410 is slid down while the basic rod 402 is held in a stable position. The sharp edge 412 of the cylinder 410 cuts out the sidewall of the hollow organ 414. After that, the cutting instrument is withdrawn, which lifts up the cutout portion 416 mounted on the pointed barbed end 408, as shown in FIG. 33.

Instruments that cut out an oval, ellipsoid, or other side-openings can be constructed in a similar manner. Cutting the ends of hollow tubular organs is a rather simple procedure, which can be accomplished by many cutting instruments already known in practice, and this is not described here.

It should be noted that openings in hollow organs can be also performed by other methods than cutting. Another method to create an opening is to pierce a hollow organ by a pointed rigid rod having external form and diameter corresponding to the form and diameter of the desired opening. This method is suitable for organs that consist predominantly of muscle tissues. The body of the pointed rigid rod pushes and displaces away the muscle fibers of the organ wall. This forms an opening in the organ without rupturing the wall and without cutting the muscle fibers, which preserves the functional capacity of the organ. In this way, connectors can be attached to the myocardial wall with a minimal damage to the heart. This is particularly important for implantation ventricular assist devices.

Figure 34:
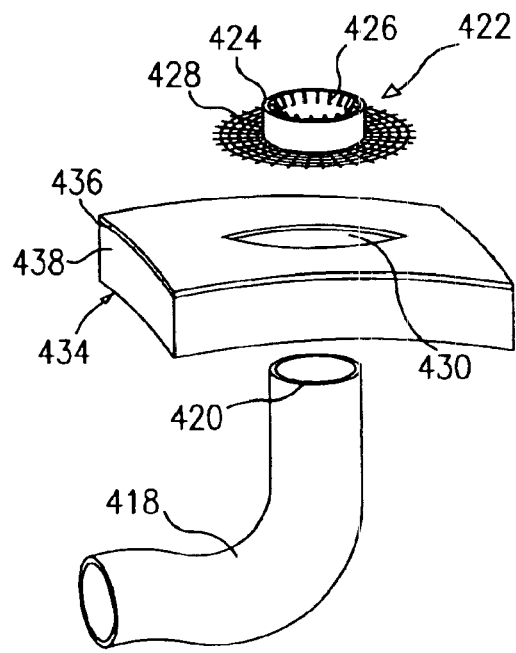
FIGS. 34 through 36 illustrate in perspective views a new method for constructing an intestinal stoma by a modified embodiment of an end connector.
Figure 35:
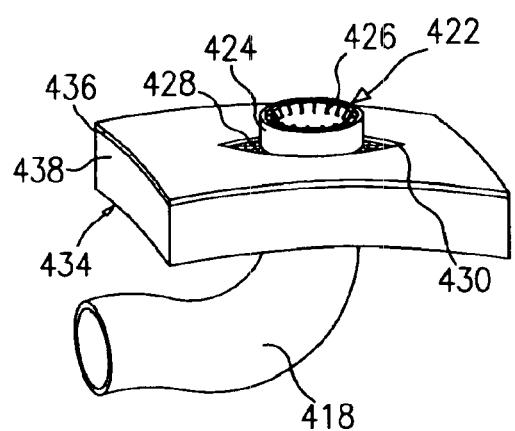
Figure 36:
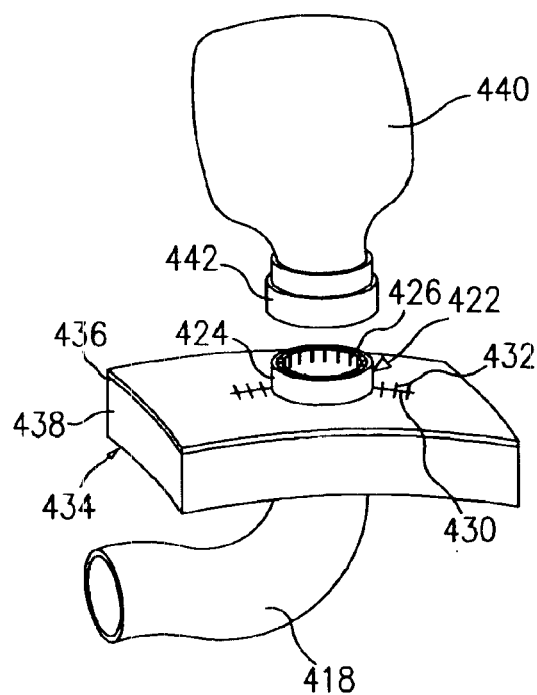

Connectors attached to hollow anatomical structure can be used for many other purposes. An example for this is shown and described next. Performing a stoma (a surgically constructed opening, especially one in the abdominal wall that permits the passage of waste after interrupting the natural passage) by a modified end connector is illustrated in FIGS. 34 through 36. The modified connector 422 has an annular rigid body 424 and multiple holding members 426. The connector 422 is further adapted with a radial wire mesh 428 attached to the lower edge of the annular body.

The surgical procedure is easy and simple to perform. The end 420 of a severed intestine 418 is drawn out through an incision 430 of the abdominal wall 434. The modified connector 422 is attached to the intestinal end 420 by the deformed holding members 426. The radial wire mesh 428 of the connector 422 is positioned between the skin 436 and the subcutaneous layers 438 of the abdominal wall 434, and the skin incision is closed with several stitches 432. A specimen bag 440 adapted with a correspondingly matching connector 442 can be coupled to the stoma.

The stoma constructed in this way has several important advantages. First, the end of the intestine is steadily kept above the skin and it can not withdraw back. Second, the radial wire mesh anchors the connector to the skin and eliminates the possibilities for formation of parastomal hernias. Third, a specimen bag can be securely attached to the intestinal end, which prevents embarrassing leaks. Fourth, the attached connector can be used to occlude the stoma by a cap for short periods. This is important for the individual when engaging in certain activities (such as sex or taking a bath), because it avoids the embarrassment from wearing a specimen bag or the risk a spontaneous intestinal leak from the stoma.

It should be noted, that instead of wire mesh, the connector could be also adapted with radial beams projecting into the subcutaneous tissues, which would be easier to remove when the constructed stoma is temporary, or it could be adapted with other means for anchoring it to the skin.

Various connectors can be constructed depending on the requirements of the anastomosis and on the tissue characteristics. When the first end of a graft is attached to a hollow organ, the surgeon has an access to the internal side of the anastomosis through the second end of the graft. In such cases, an indivisible union connector, formed by a consolidation of two annular rigid bodies of two connectors, can find beneficial application.

Figure 37A:
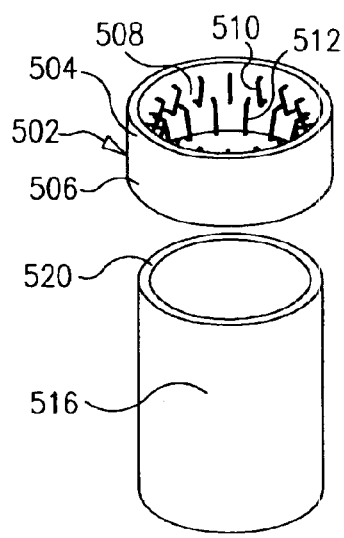
FIGS. 37A, 37B, and 37C illustrate an indivisible union connector positioned above a hollow anatomical structure. They are shown in a perspective view in FIG. 37A. The same connector and hollow structure crosscut in half are shown in a perspective view in FIG. 37B. A portion of them (encircled by window C* in FIG. 37B) is shown magnified in a schematic front view in FIG. 37C.
Figure 37B:
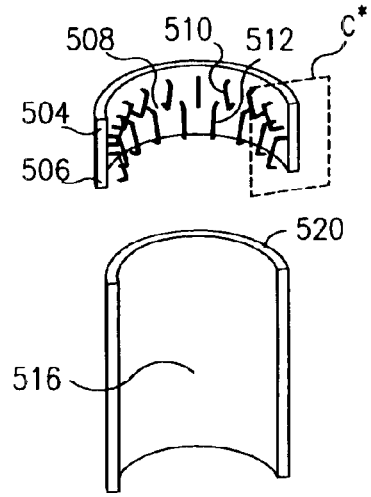
Figure 37C:
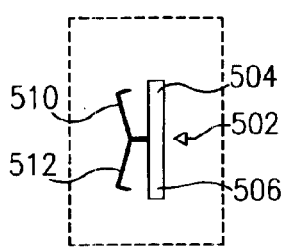
Figure 38A:
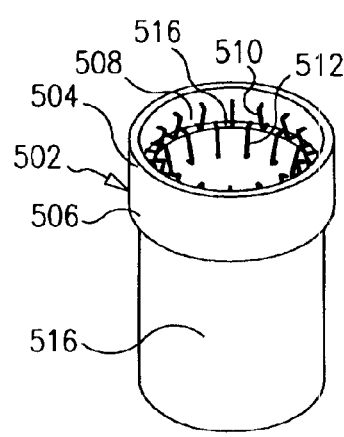
FIGS. 38A, 38B, and 38C illustrate the union connector positioned over the end of the hollow structure. They are illustrated in the same views as in FIGS. 1A, 1B, and 1C respectively.
Figure 38B:
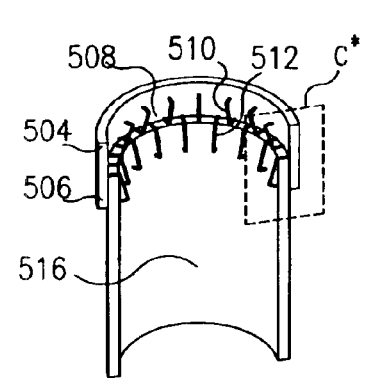
Figure 38C:
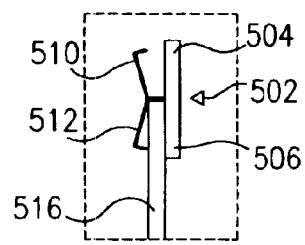
Figure 39A:
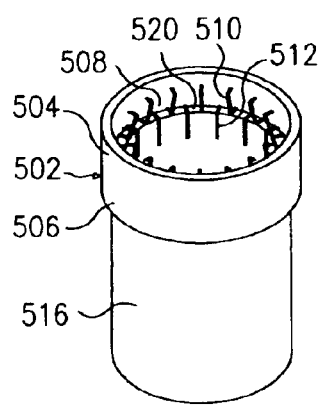
FIGS. 39A, 39B, and 39C illustrate the union connector attached to the end-opening of the hollow structure. They are illustrated again in the same views as in the previous figures.
Figure 39B:
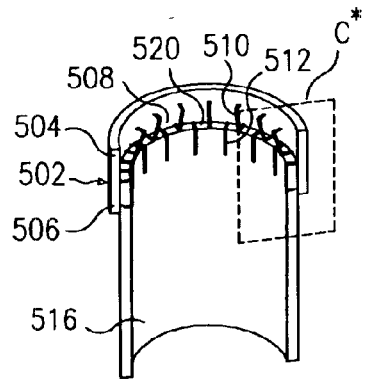
Figure 39C:
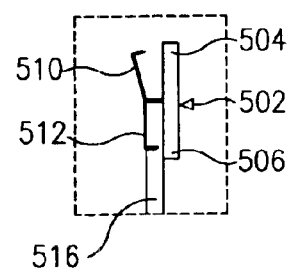
Figure 40A:
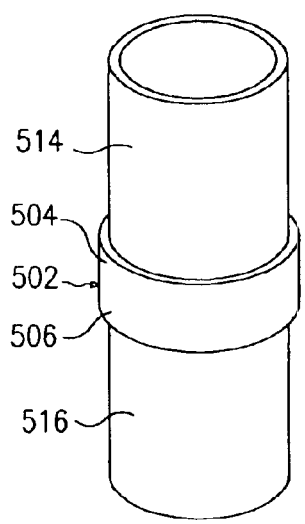
FIGS. 40A, 40B, and 40C illustrate end-to-end anastomosis accomplished with the union connector attached the ends of two hollow structure in the same view as in the previous figures.
Figure 40B:
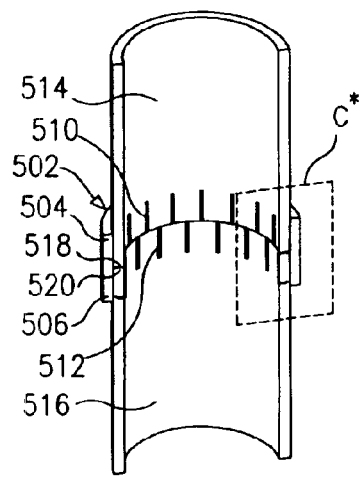
Figure 40C:
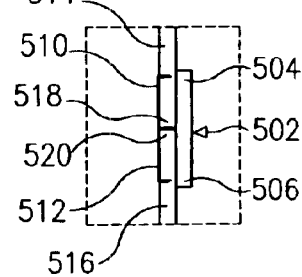

An indivisible union connector for end-to-end anastomosis illustrated in FIGS. 37A through 40C. Figures "A" show in perspective view the whole union connector and hollow organs, figures "B" shows the same elements crosscut in half in the same perspective views, and figures "C" are schematic illustrations of a portion of them as defined by the C* windows in figures "B". In FIG. 37 the union connector is shown above one of the two hollow organs, FIG. 38 it is shown positioned over the hollow organ, in FIG. 39 it is shown attached to the hollow organ, and in FIG. 40 it is shown attached to end of both organs.

The indivisible union connector 502 consists of a first annular rigid portion 504 and a second annular rigid portion 506, which actually constitutes the consolidated annular bodies of two end connectors. The union connector has first holding members 510 and second holding members 512, which are actually the respective holding members of the consolidated connectors. The consolidated first annular portion 504 and second annular portion 506 form an inner fluidproof surface 508 that surrounds the cut-edges 518 and 520 of respective first hollow structure 514 and second hollow structure 516.

Accomplishing an end-to-end anastomosis with the indivisible union connector is a similar to performing it with two end connectors. As shown here, the union connector 502 is positioned over the wall of a second hollow structure 516. The second holding members 512 are then deformed to press the hollow structure 516 towards the outer second annular portion 506. After that in the same way the first hollow structure 514 is affixed to the first annular portion 504 of the union connector by the first holding members 510. The fluidproof surface 508 of the union connector 502 surrounds the two approximated structures and does not permit a leak out of their abutted cut-edges 518 and 520. In this way an end-to-end anastomosis is completed fast, easy, and securely.

The end-to-end anastomosis with the indivisible union connector is similar to the end-to-end anastomosis by two coupled end connectors. In the same way, the ends of the two hollow structures are precisely approximated with abutted cut-edges of their wall-openings. This positions the external, medium, and internal layers of the two walls in direct contact facing each other. Same layers of the two vessels meet and reconnect with each other. The hollow anatomical structures heal in a layer specific manner, which cannot be accomplished by other anastomosing devices.

When anastomosing blood vessels, foreign material in contact with the blood flow should be reduced to minimize risk of thrombus formation. Additional means for preventing blood vessels displacing axially out of the connectors might be needed for medium and large vessels, which conduct blood under high pressure.

Figure 41A:
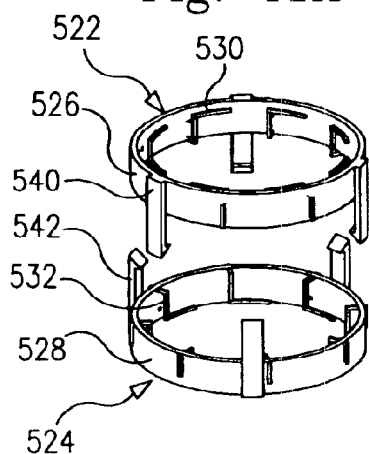
FIGS. 41A and 41B illustrate a different embodiment of end connectors shown in perspective view in FIG. 41A, the same elements crosscut in half in the same perspective view in FIG. 41B.
Figure 41B:
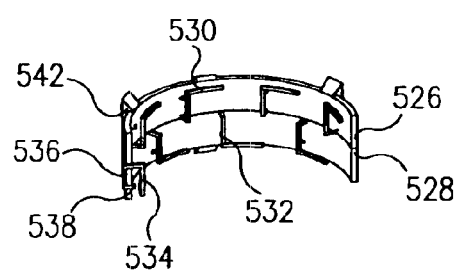
Figure 42A:
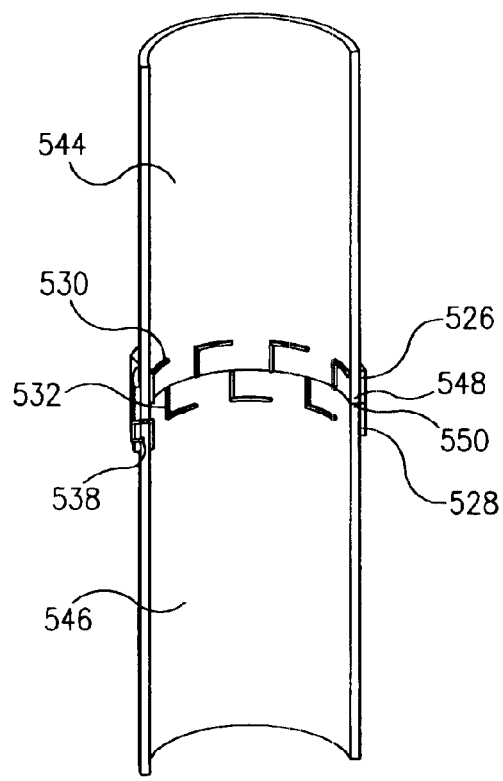
FIGS. 42A and 42B illustrate and end-to-end anastomosis performed by the union of above connectors, showing it crosscut in half in perspective view in FIG. 42A, and whole in the same perspective view in FIG. 42B.
Figure 42B:
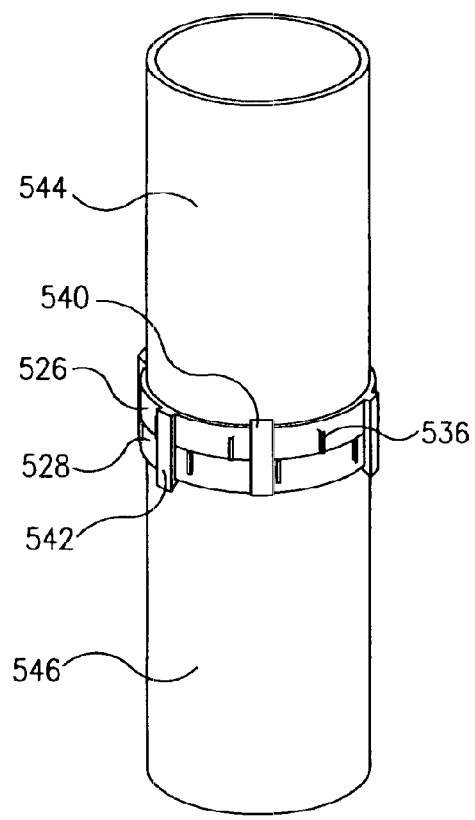

A different embodiment of coupling end connectors adapted for application with medium and large blood vessels, and a method for their manufacture are illustrated in FIGS. 41A through 42B. FIG. 41A shows two end connectors in perspective view. The same connectors crosscut in half are shown in FIG. 41 B. FIG. 42A demonstrates end-to-end anastomosis performed by the union of the two end connectors showing them crosscut in half in perspective view, and the same elements whole in the same view are shown in FIG. 42B.

The two end connectors, first end connector 522 and second end connector 524, are identical. They consist respectively of: first annular rigid body 526 and second annular rigid body 528; first holding means 530 and second holding means 532; first coupling plates 540 and second coupling plates 542. They are respectively attached to first blood vessel 544 and second blood vessel 546.

Performing an end-to-end anastomosis is accomplished in the already described manner—attaching first connector 522 to first blood vessel 544 and second connector 524 to second blood vessel 546, then coupling the attached connectors in a union. This creates a fluidproof surface that surrounds the abutted cut-edges 548 and 550 of first and second blood vessel respectively. Once again, the approximated ends of the two vessels are abutted with cut-edges of their openings, which allows a layer specific healing of their walls.

The holding members of this embodiment are designed to adapt to the specific requirements of large arterial blood vessels—less foreign material within the blood flow, and a necessity to prevent axial displacement of the adjoined vessel. Each holding member is made of a thin metal wire. It has an internal "L" shape portion 534 that presses the vessel to the annular rigid body. Through a small hole in the annular body, the wire exits out and turns into a short external portion 536 that runs axially to the middle and through a small hole enters back the annular body. The wire ends in a short radially pointed portion 538. This radial portion penetrates the wall of the blood vessel and prevents axial displacement.

This configuration of the holding means allows for easy manufacture of the end connector. First, two small holes are drilled on the annular body. Then the ends of a "U" shaped wire are threaded from outside into the holes and the short external portion is welded. After that one wire end is formed in a "L" shape holding member and the other end is cut to create the short radial portion.

Figure 43A:
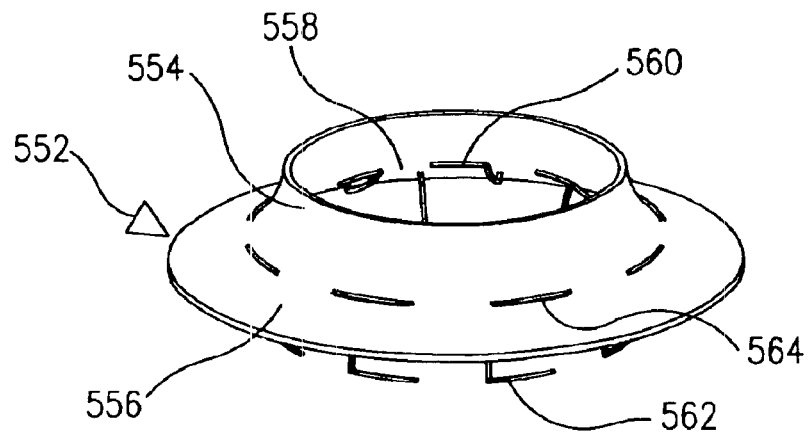
FIGS. 43A, 43B, and 43C illustrate an indivisible union connector for side-to-end anastomosis in perspective top, perspective bottom, and crosscut perspective bottom views respectively.
Figure 43B:
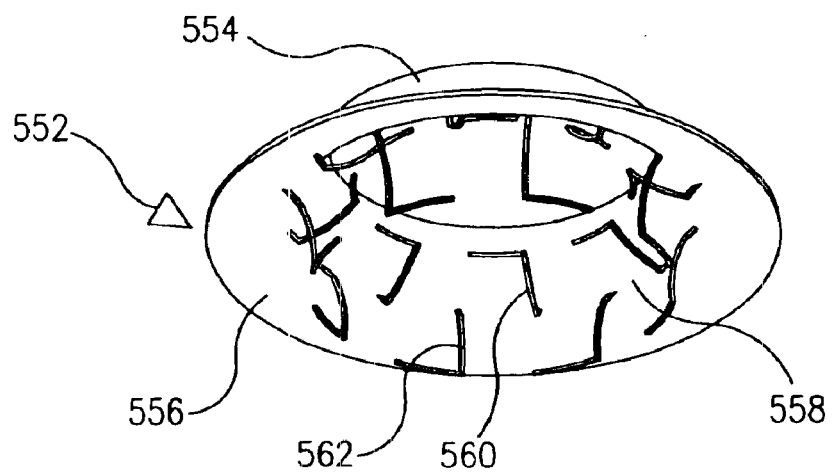
Figure 43C:
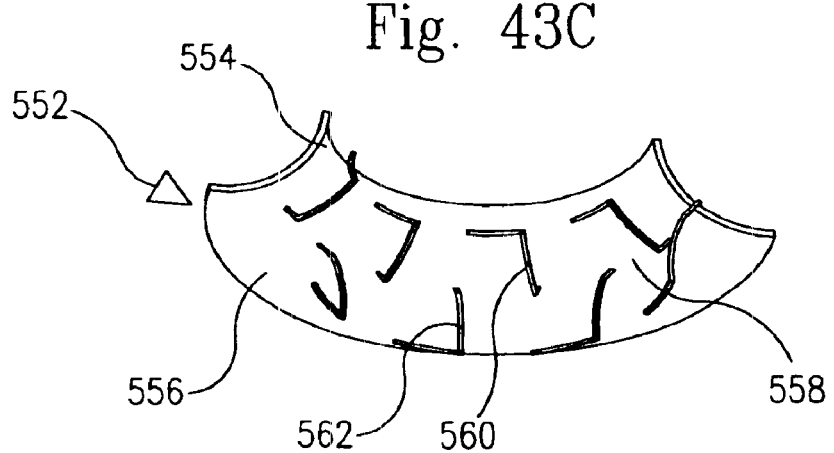

Another embodiment of an indivisible union connector for side-to-end anastomosis that can be particularly advantageous for vascular graft anastomoses, such as the aortic anastomosis of a coronary bypass graft, is shown in FIGS. 43A through 46B. FIG. 43A is a perspective top view of the connector. FIGS. 43B and 44C are perspective bottom views of the connector showing it whole and crosscut in half respectively.

The union connector 552 consists of a first annular rigid portion 554 and second annular rigid portion 556 that are seamlessly consolidated. It has an inner fluidproof surface 558. First holding members 560 and second holding members 562 are affixed to the union connector. Both of them have "L" shape form. The first holding members 560 are aimed upward to accept the end of the first blood vessel 566. The second holding members 562 are aimed downward so they can be inserted in the side-opening of the second blood vessel 568. Each pair of adjacent first and second holding members are manufactured from a single wire and are interconnected on the outside by transverse portion 564 that is welded to the outside of the connector.

Figure 44A:
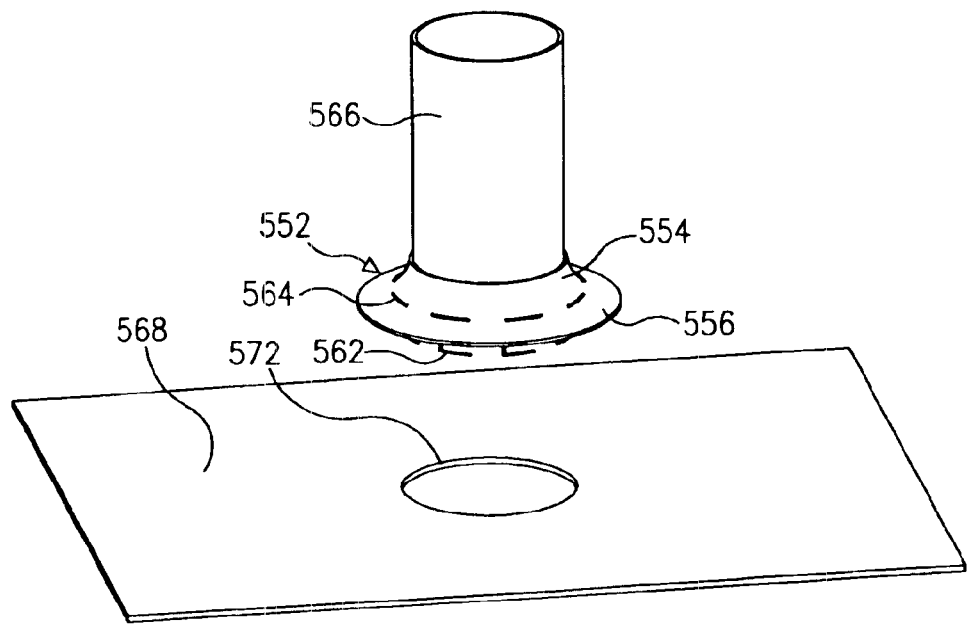
FIGS. 44A and 44B illustrate the union side-to-end connector attached to the end of a hollow structure in perspective top and perspective bottom views respectively.
Figure 44B:
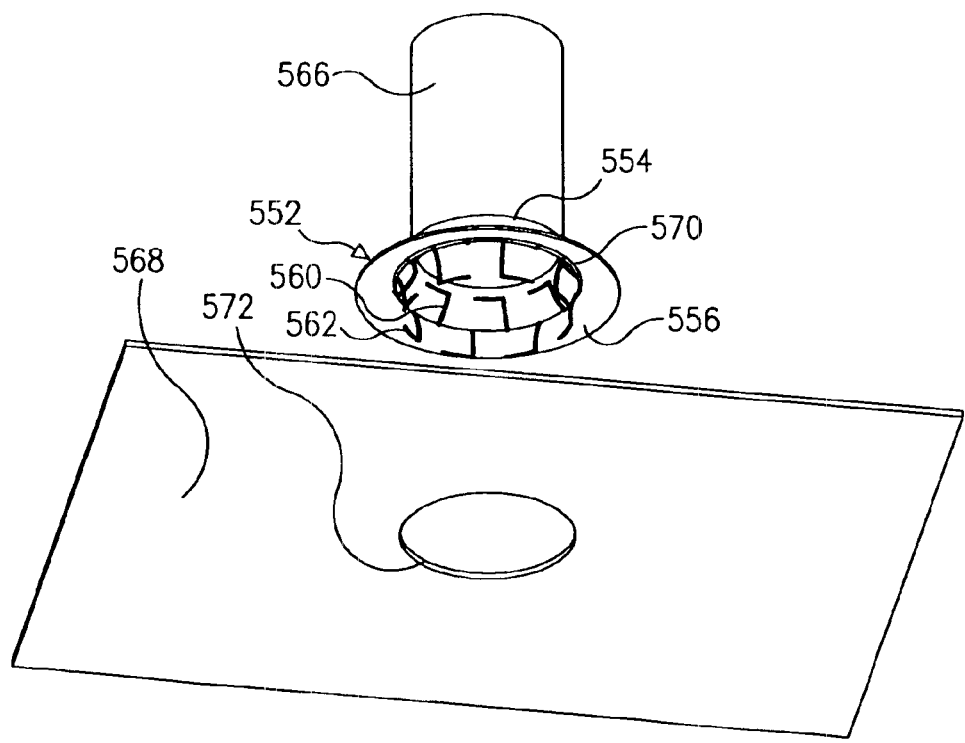
Figure 45A:
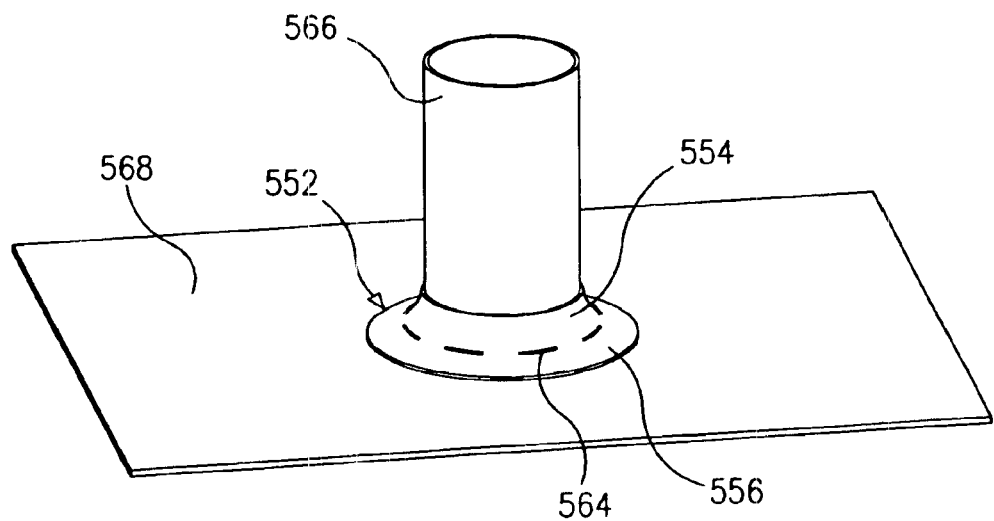
FIGS. 45A and 45B illustrate the union side-to-end connector of attached to the end of a hollow structure and positioned over the side-opening of another hollow structure in a perspective top and perspective bottom views respectively
Figure 45B:
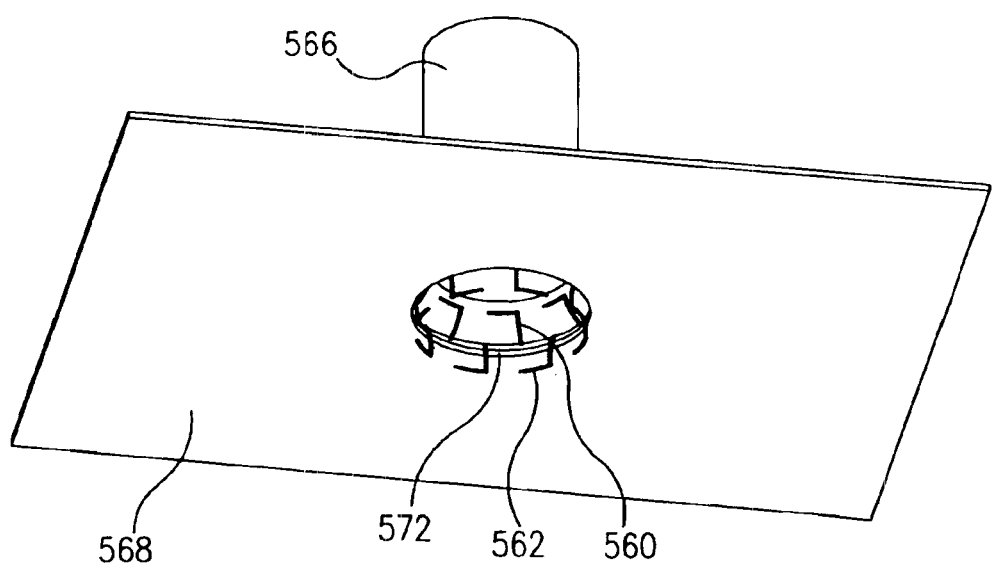

The union connector 552 attached to the end of first vessel 566 by deformed first holding members 560 is shown in top perspective view in FIG. 44A and in bottom perspective view in FIG. 44B. In the following two FIGS. 45A and 45B, the union connector 552 is illustrated in the same views attached to the first vessel 566 and positioned over the sidewall of the second vessel 568 so the second holding members 562 protrude along cut-edges 572 of the side-opening into the second vessel 568. In the case of a coronary bypass graft anastomosis to the aorta, the second vessel (aorta) is much larger than the first vessel and the anastomosis is performed to a lightly arcuate surface that is illustrated as a flat surface for better clarity in the drawings. After the connector 552 is positioned over the side-opening of the second vessel 568, the second holding members 562 are deformed to press the sidewall of the second vessel toward the second annular portion of the union connector.

Figure 46A:
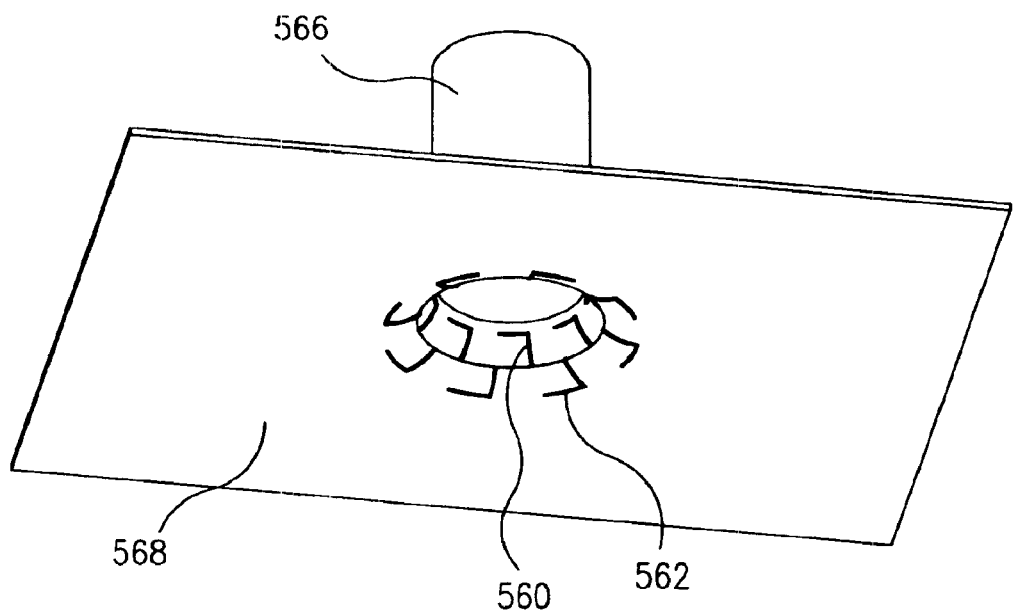
FIGS. 46A and 46B illustrate a side-to-end anastomosis of two hollow structures by the union side-to-end connector shown in perspective bottom and in a perspective bottom crosscut view respectively.
Figure 46B:
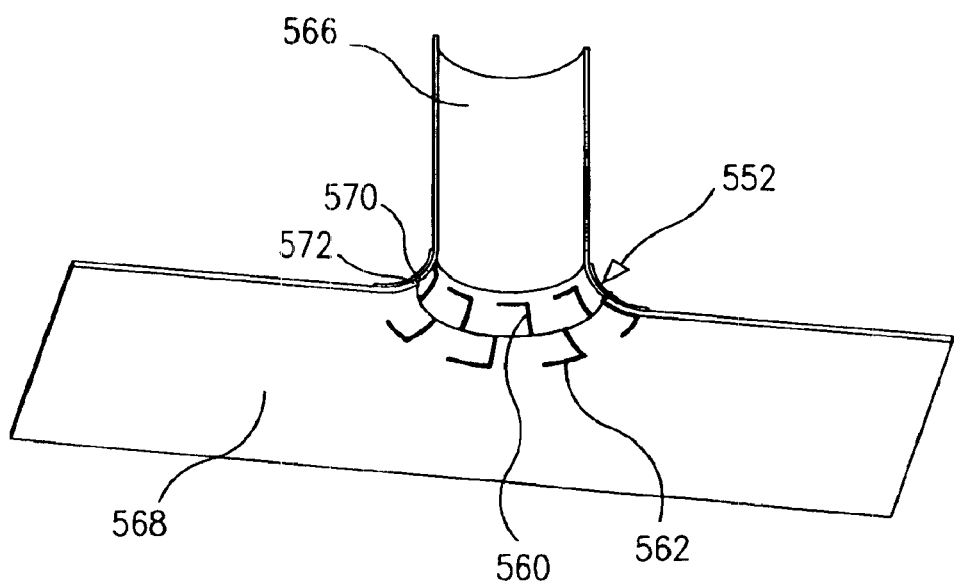
Figure 47A:
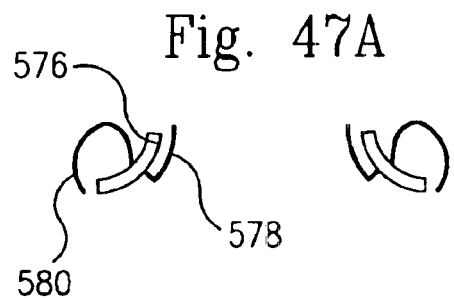
FIGS. 47A and 47B are schematic illustrations of a different embodiment of a side-to-end union connector showing it with open and deformed holding members.
Figure 47B:
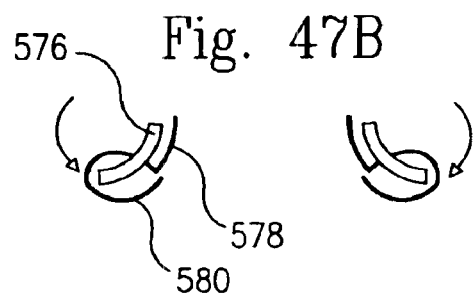
Figure 48:
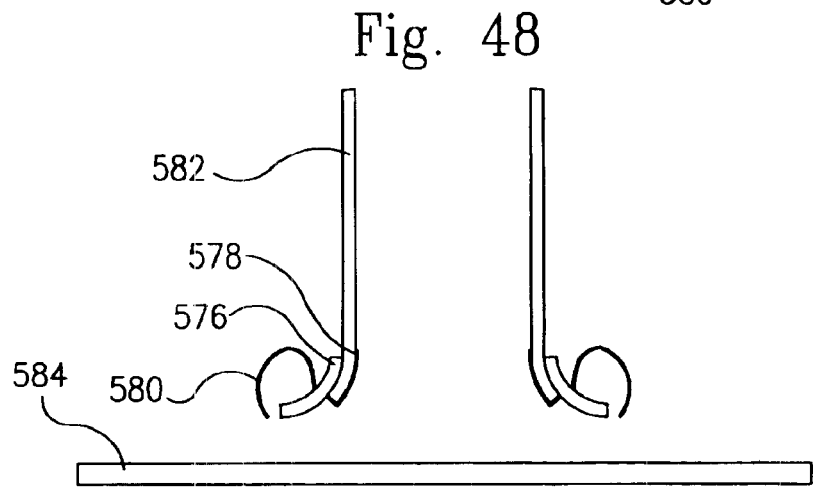
FIG. 48 is a schematic illustration showing the union side-to-end connector attached to the end of the first hollow structure.

A completed side-to-end anastomosis is shown in top perspective view in FIG. 46A and crosscut in half in a bottom perspective view in FIG. 46B. As seen, the two vessel walls are exactly approximated. Their cut-edges 570 and 572 abut exactly each other, which allows a layer specific healing of the same layers of both vessels. The inner fluidproof surface 558 surrounds the abutted cut edges 570 and 572 of the anastomosed walls and prevents leaks out of the anastomosis.

Another embodiment of an indivisible union connector for side-to-end vascular anastomoses is illustrate in schematic drawings in FIGS. 47A through 49. The union connector has a structure similar to the last described connector embodiment and will be briefly discussed. The indivisible union connector 576 has first holding members 576 for accepting the end of the first blood vessel 582 and second holding members 580 for accepting the side of the second blood vessel 584.

The second holding members 580 are notably different. Their shape is predefined so when they are deformed, as shown with arrows in FIG. 47B, they bend down and pierce the sidewall of the vessel 584 away from the anastomotic line. Further deformation bends them inward and they press the sidewall towards the rigid body of the outside connector. This is an important feature as it allows a closed anastomosis to be performed. The union connector 576 attached to the end of the first vessel 584 can be attached to the sidewall of the second vessel 586 before performing an opening in the second vessel. This can be beneficial in cases when clamping of the side vessel should be preferably avoided.

Figure 49:
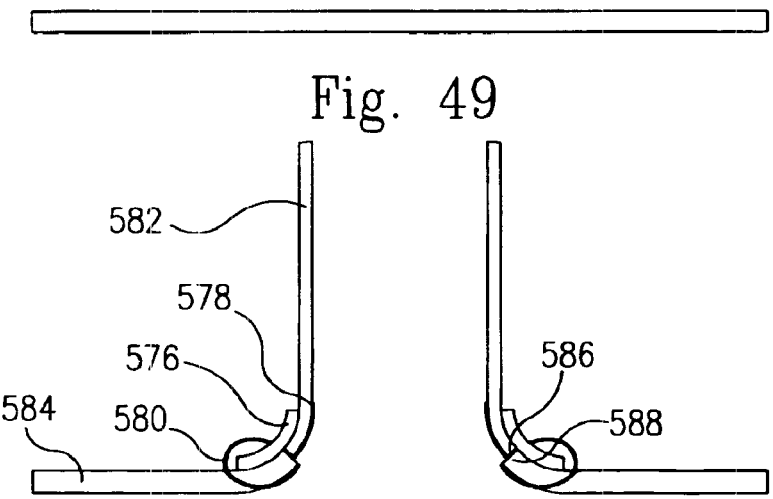
FIG. 49 is a schematic illustration showing a side-to-end anastomosis performed by the union side-to-end connector.

The side-to-end anastomosis performed by the indivisible union connector 576 is illustrated in FIG. 49. As seen, cut-edges 586 and 588 of approximated first and second blood vessels 582 and 584 are again precisely abutted and surrounded by the inner fluidproof surface of the union connector.

Intestines have relatively thicker walls than other hollow body organs. Their walls are fragile and sutures can easily cut through. In cases of intestinal obstructions and infections, their walls swell and become extremely fragile. Anastomosing swollen intestines is an extremely risky procedure that can be complicated by serious and sometimes fatal consequences. In many of these cases, surgeons avoid anastomoses and interrupt the intestinal passage with an intestinal stoma.

Figure 50A:
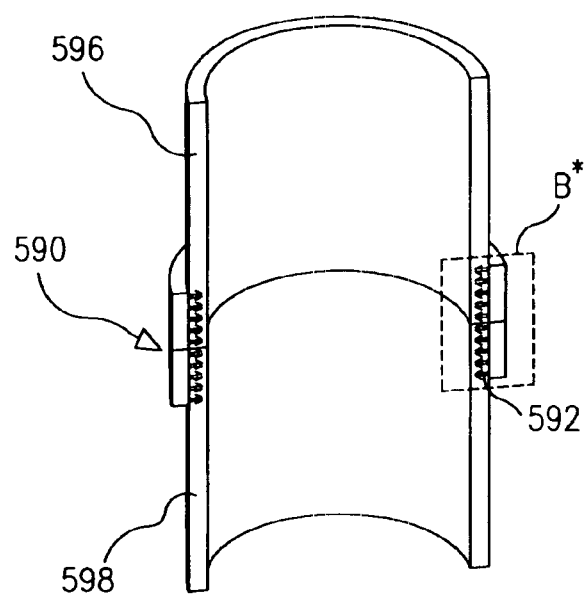
FIGS. 50A and 50B illustrate an embodiment of a union connector for end-to-end anastomosis of intestinal organs, showing it in a crosscut perspective view and a magnified schematic view respectively.
Figure 50B:
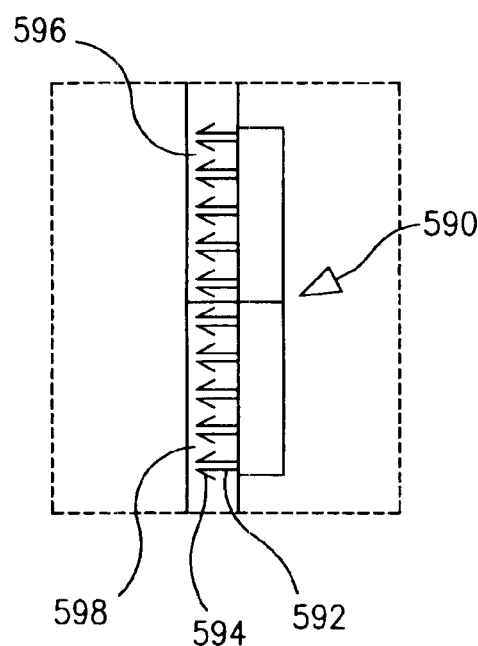

Another embodiment of a union connector that could find beneficial application for end-to-end anastomosis of gastrointestinal organs is shown in FIGS. 50A and 50B. Two intestinal organs 596 and 598 anastomosed by a union connector 590 are shown crosscut in perspective view in FIG. 50A. A portion of them defined by window B* is shown magnified in a schematic view in FIG. 50B.

The annular rigid body of the union connector 590 is similar to embodiments already described above. A different type of holding members 592 are used in this case to keep the intestinal walls adjoined to the internal surface of the connector 590. Each one of the holding members 592 is pointed radially inward and has a barbed portion 594. Intestinal walls are attached to the connector by pressing the walls outward over the radially pointed holding members 592. The holding members penetrate the intestinal walls. Their barbed portions prevent the walls of moving way from the inner surface of the connector.

When compared to manual suturing, the intestinal walls are held by much higher number of holding members than sutures. Their holding force is evenly distributed on the anastomosed walls. This substantially reduces the risk of cutting through.

The process of intestinal healing is naturally quick and efficient. No additional forces are needed to support the intestinal anastomosis once the healing is completed. For that reason, materials that are absorbed by the body can be preferably used to manufacture intestinal connectors. Other different shapes of holding members, such as shapes used for Velcro attachments, can be used for the same purpose as well.

It should be also noted, that the connector of the present invention can be attached to other hollow structures that have different external surfaces. In a similar manner as described above, it can be attached to surfaces that are flat, spherical, conical, or irregular. The scull, the thorax, and the abdomen, which form respective body cavities, should be also construed as hollow structures to which the connector can be attached.

In should be also noted, that in a reciprocal manner the connector of the present invention can also be attached to the internal surfaces of hollow anatomical organs.

It should be also further noted that the connector of the present invention can also be used for many other surgical procedures. It can be used for anastomosing hollow anatomical organs by artificial or natural grafts, for bypass procedures, for transplant procedures, or for implantation of ventricular assist devices or total artificial hearts. It can be also used as a port entrance through which catheters, drains, or other conducting tubes are inserted securely into a body organ or cavity for diagnostic, therapeutic, or nutritional purposes.

The foregoing description of the principles of operation of the preferred embodiments of the connector for hollow anatomical organs made in conjunction with the various figures of the drawings are intended to be illustrative of the practice of the invention. Without departing from the principles of operation of the present invention, other embodiments and variations can be utilized, as described above.

Thus, the information disclosed in the description of the present invention is intended to be representative of the described principles. And as certain changes may be made without departing from the scope of the invention, it is intended that all matter contained in the above description or shown in the accompanying drawings shall be interpreted as illustrative, but not in a limiting sense. It is also to be understood, that the following claims are intended to cover all of the generic and specific features of the invention herein described and all statements of the scope of the invention which, as a matter of language, might be said to fall therebetween.

What is claimed is:

1. A connector for joining a hollow anatomical structure to another hollow structure, said connector comprising:

a first annular rigid body with an inner surface conformed reciprocally to an outer surface surrounding a wall-opening of a first hollow structure, said annular rigid body provided with first holding means that in open configuration are inserted into said wall-opening of said first hollow structure without distorting its shape, said first holding means capable of being transformed by effecting means in a closed configuration in which said first holding means press said first hollow structure towards said inner surface of said first annular body thus affixing said first hollow structure to said first annular body, wherein coupling of the affixed first annular body to a second annular rigid body affixed to a second hollow structure forms a fluid-proof surface encircling the abutted edges of the wall-openings of the approximated first and second hollow structures.

2. The connector in claim 1, wherein said connector further comprising coupling means for joining in a fluid-proof union said first annular body with said second annular body.

3. The connector in claim 2, wherein said connector further comprising means for preventing axial displacement of first structure affixed to said fist annular body.

4. The connector in claim 2, wherein said inner fluid-proof surface further comprising a porous layer into which bodily tissues can grow in.

5. A connector for joining a hollow anatomical structure to another hollow structure, said connector comprising:

(a) a fluid-proof surface formed by a union of a first annular rigid body with a second annular rigid body, said first annular body with an inner surface conformed to an outer surface surrounding a wall-opening of a first hollow structure, and said second annular body with an inner surface conformed to an outer surface surrounding a wall-opening of a second hollow structure, said fluid-proof surface enclosing said first hollow structure and second hollow structures abutted with edges of their wall-openings;

(b) first holding means that in an opened configuration are inserted into said wall-opening of said first hollow structure without distorting its shape, said first holding means capable of being transformed by effecting means to a closed configuration in which said first holding means press said first hollow structure towards said inner surface of said first annular body thus affixing said first hollow structure to said fluid-proof surface of said connector; and (c) second holding means capable of keeping said second hollow structure affixed to said inner fluid-proof surface of said connector.

6. The connector in claim 5, wherein said first annular body and said second annular body are consolidated in a seamless union.

7. The connector in claim 6, wherein said connector further comprising means for preventing axial displacement of at least one of the affixed hollow structures.

8. The connector in claim 6, wherein said fluid-proof surface further comprising a porous layer into which bodily tissues can grow in.

9. The connector in claim 5, wherein said connector further comprising coupling means for joining said first annular body with said second annular body in a fluid-proof union.

10. The connector in claim 9, wherein said connector further comprising means for preventing axial displacement of at least one of the affixed hollow structures.

11. The union connector in claim 9, wherein said fluid-proof surface further comprising a porous layer into which bodily tissues can grow in.

12. A union connector for joining a hollow anatomical structure to another hollow structure, said connector comprising:

(a) an annular rigid body with an inner fluid-proof surface conformed to enclose outer surfaces of a first hollow structure and a second hollow structure abutted with cut-edges of their wall-openings;

(b) first holding means that in an opened configuration are inserted into the wall-opening of said first hollow structure, said first holding means capable of being transformed by effecting means to a closed configuration in which said first holding means press said first hollow structure towards said fluid-proof surface of said annular rigid body thus keeping said first hollow structure affixed to said connector; and (c) second holding means capable of keeping said second hollow structure affixed to said inner fluid-proof surface of said union connector.

13. The union connector in claim 12, wherein said fluid-proof surface is formed by a union of a first annular rigid body with a second annular rigid body, said first annular body with an inner surface conformed to an outer surface around a wall-opening of said first hollow structure, and said second annular body with an inner surface conformed to an outer surface around a wall-opening of said second hollow structure.

14. The union connector in claim 13, wherein said first annular body and said second annular body are consolidated in a seamless union.

15. The union connector in claim 14, wherein said connector further comprising means for preventing axial displacement of at least one of the adjoined hollow structures.

16. The union connector in claim 14, wherein said fluid-proof surface further comprising a porous layer into which bodily tissues can grow in.

17. The union connector in claim 13, wherein said connector further comprising coupling means for joining said first annular body with said second annular body in a fluid-proof union.

18. The union connector in claim 17, wherein said connector further comprising means for preventing axial displacement of at least one of the adjoined hollow structures.

19. The union connector in claim 17, wherein said fluid-proof surface further comprising a porous layer into which bodily tissues can grow in.

20. A method for joining a hollow anatomical structure to another hollow structure, said method comprising the steps of:

(a) providing a first connector with a first annular rigid body with an inner surface conformed to surround an outer surface of a wall-opening of a first hollow structure;

(b) attaching said first annular body to said first hollow structure by first holding means that in an open configuration are inserted into said wall-opening of said first hollow structure and then by effecting means said first holding means are transformed in a second configuration in which they press said first hollow structure toward said first annular body this affixing said first hollow structure to said first annular body; and (c) joining in a union said first annular body of said first connector with a second annular rigid body of a second connector attached to a second hollow structure and forming a fluid-proof surface that surrounds the abutted cut-edges of the wall openings of approximated first and second hollow structures.

21. The method for joining of claim 20, wherein said step of attaching said first annular body to said first hollow structure further comprising the step of growing of bodily tissues into said fluid-proof surface of said first annular body.

22. A method for joining two hollow anatomical structures, said method comprising the steps of:

(a) providing a union connector comprising an annular rigid body with an inner fluid-proof surface predefined to surround outer surfaces of a first hollow structure and a second hollow structure abutted with cut-edges of their wall-openings;

(b) attaching said union connector to said first hollow structure by first holding means that in an open configuration are inserted into said first hollow structure and then by effecting means are transformed in a second configuration in which said holding means press said first hollow structure towards said fluid-proof surface thus affixing said first hollow structure to said union connector; and (c) attaching said union connector to said second hollow structure by second holding means keeping said second hollow structure affixed to said annular body in a manner that said inner fluid-proof surface of said connector encloses the abutted cut-edges of the approximated first and second hollow structures.

23. The method for joining of claim 22, wherein said steps of attaching said first and second hollow structures to said fluid-proof surface of said annular body further comprising the step of growing of bodily tissues into said fluid-proof surface of said connector.

* * * * *